(12) United States Patent
McGowan et al.

(10) Patent No.: US 11,858,913 B2
(45) Date of Patent: Jan. 2, 2024

(54) BICYCLIC PYRIDAZINONES AND METHODS OF USE THEREOF

(71) Applicant: ALIGOS THERAPEUTICS, INC., South San Francisco, CA (US)

(72) Inventors: David Craig McGowan, Brussels (BE); Pierre Jean-Marie Bernard Raboisson, Wavre (BE); Koen Vandyck, Beringen (BE); Jerome Deval, El Granada, CA (US); Leonid Beigelman, San Mateo, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/520,176

(22) Filed: Nov. 5, 2021

(65) Prior Publication Data

US 2022/0144811 A1 May 12, 2022

Related U.S. Application Data

(60) Provisional application No. 63/110,816, filed on Nov. 6, 2020.

(51) Int. Cl.
*C07D 401/14* (2006.01)
*C07D 403/12* (2006.01)

(52) U.S. Cl.
CPC ......... *C07D 403/12* (2013.01); *C07D 401/14* (2013.01)

(58) Field of Classification Search
CPC ............................ C07D 401/14; C07D 403/12
See application file for complete search history.

(56) References Cited

FOREIGN PATENT DOCUMENTS

| CN | 111484481 A | 8/2020 |
|---|---|---|
| CN | 113549058 A | 10/2021 |
| EP | 4 050 008 A1 | 8/2022 |
| WO | WO-2007/009913 A1 | 1/2007 |
| WO | WO-2019/240938 A1 | 12/2019 |
| WO | WO-2020/123827 A1 | 6/2020 |
| WO | WO-2020/228577 A1 | 11/2020 |
| WO | WO-2020/239076 A1 | 12/2020 |
| WO | WO-2021/050945 A1 | 3/2021 |
| WO | WO-2021/078274 A1 | 4/2021 |
| WO | WO-2021/121210 A1 | 6/2021 |

OTHER PUBLICATIONS

Anderson et al., "Cycloadditions of Noncomplementary Substituted 1,2,3-Triazines," Org. Lett., 2014, 16:5084-5087.
Anderson et al., "Inverse Electron Demand Diels-Alder Reactions of 1,2,3-Triazines: Pronounced Substituent Effects on Reactivity and Cycloaddition Scope," J. Am. Chem. Soc., 2011, 133:12285-12292.
Bookout et al., "Anatomical Profiling of Nuclear Receptor Expression Reveals a Hierarchical Transcriptional Network," Cell, Aug. 25, 2006, 126(4):789-799.
Chalasani et al., "The Diagnosis and Management of Non-alcoholic Fatty Liver Disease: Practice Guideline by the American Gastroenterological Association, American Association for the Study of Liver Diseases, and American College of Gastroenterology," Gastroenterology, 2012, 142(7):1592-1609.
Drummond et al., "Evaluation and Synthesis of Aminohydroxyisoxazoles and Pyrazoles as Potential Glycine Agonists," J. Med. Chem., 1989, 32(9):2116-2128.
Dulai et al., "Increased Risk of Mortality by Fibrosis Stage in Nonalcoholic Fatty Liver Disease: Systematic Review and Meta-Analysis," Hepatology, May 2017, 65(5):1557-1565.
Erion et al., "Targeting thyroid hormone receptor-B agonists to the liver reduces cholesterol and triglycerides and improves the therapeutic index," PNAS, Sep. 25, 2007, 104(39):15490-15495.
Flamant et al., "International Union of Pharmacology. LIX. The Pharmacology and Classification of the Nuclear Receptor Superfamily: Thyroid Hormone Receptors," Pharmacological Reviews, 2006, 58(4):705-711.
Haning et al., "Novel heterocyclic thryomimetics," Bioorganic & Medicinal Chemistry Letters, Apr. 1, 2005, 15(7):1835-1840.
Hartley et al., "A Thyroid Hormone-Based Strategy for Correcting the Biochemical Abnormality in X-Linked Adrenoleukodystrophy," Endocrinology, May 2017, 158(5):1328-1338.
Harvey et al., "Mechanism of Thyroid Hormone Action," Thyroid, Jun. 2002, 12(6):441-446.
Hirano et al., "Thyromimetics: a review of recent reports and patents (2004-2009)," Expert Opin. Ther. Pat., Feb. 2010, 20(2):213-228.
Iikuni et al., "Development of the 99mTc-Hydroxamamide Complex as a Probe Targeting Carbonic Anhydrase IX," Molecular Pharmaceutics, 2019, 16(4):1489-1497.
Katane et al., "Identification of Novel D-Amino Acid Oxidase Inhibitors by in Silico Screening and Their Functional Characterization in Vitro," J. Med. Chem., 2013, 56(5):1894-1907.
Kowalik et al., "Thyroid Hormones, Thyromimetics and Their Metabolites in the Treatment of Liver Disease," Frontiers in Endocrinology, Jul. 10, 2018, 9:382, 11 pages.
Lazo et al., "Nonalcoholic Fatty Liver disease (NAFLD): Is It Really a Serious Condition?", Hepatology, Oct. 2012, 56(4):1580-1584.

(Continued)

*Primary Examiner* — Brian E McDowell
(74) *Attorney, Agent, or Firm* — Foley & Lardner LLP

(57) ABSTRACT

Disclosed herein are compounds of Formula I:

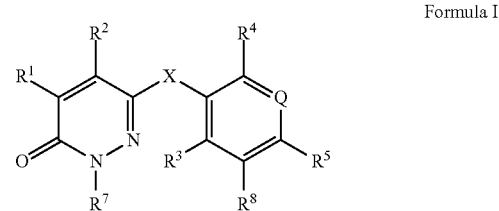

Formula I or a stereoisomer or a tautomer thereof, or a pharmaceutically acceptable salt thereof, pharmaceutical compositions comprising such compounds, and methods of treating disease by administering or contacting a subject with one or more of the above compounds.

18 Claims, No Drawings

(56) References Cited

OTHER PUBLICATIONS

Liljebris et al., "Investigation of Potential Bioisosteric Replacements for the Carboxyl Groups of Peptidomimetic Inhibitors of Protein Tyrosine Phosphatase 1B: Identification of a Tetrazole-Containing Inhibitor with Cellular Activity," J. Med. Chem. 2002, 45(9):1785-1798.
Milanesi et al., "Beam Me In: Thyroid Hormone Analog Targets Alternative Transporter in Mouse Model of X-Linked Adrenoleukodystrophy," Endocrinology, May 2017, 158:1116-1119.
Sakya et al., "Preparation and Inverse Electron Demand Diels-Alder Reactions of 3-Methyoxy-6-methylthio-1,2,4,5-tetrazine," Tetrahedron Letters, 1997, 38(22):3805-3808.
Serfaty et al., "Definition and natural history of metabolic steatosis: clinical aspects of NAFLD, NASH and cirrhosis," Diabetes and Metabolism, 2008, 34:634-637.
Sorensen et al., "A Novel Route to 5-Substituted 3-Isoxazolols. Cyclization of N,O-DiBoc Beta-keto Hydroxamic Aids Synthesized via Acyl Meldrum's Acids," J. Org. Chem., 2000, 65(4):1003-1007.
Ushkov et al., "Rational Catalysis Design on the Basis of Mechanistic Understanding: Highly Efficient PD-Catalyzed Cyanation of Aryl Bromides with NaCN in Recyclable Solvents," J. Am. Chem. Soc., 2011, 133:10999-11005.
Younossi et al., "Current and Future Therapeutic Regimens for Nonalcoholic Fatty Liver Disease and Nonalcoholic Steatohepatitis," Hepatology, Jul. 2018, 68(1):361-371.
Younossi et al., "Global Epidemiology of Nonalcoholic Fatty Liver Disease—Meta-Analytic Assessment of Prevalence, Incidence and Outcomes," Hepatology, Jul. 2016, 64(1):73-84.
International Search Report and Written Opinion dated Feb. 22, 2022 in PCT PCT/US2021/058320.

BICYCLIC PYRIDAZINONES AND METHODS OF USE THEREOF

CROSS-REFERENCE TO RELATED APPLICATIONS

This application claims the benefit of priority to U.S. Provisional Patent Application Ser. No. 63/110,816, filed on Nov. 6, 2020, the entire disclosure of which is hereby incorporated by reference herein.

FIELD OF THE DISCLOSURE

The present disclosure is in the field of pharmaceutical compounds and preparations and method of their use in the treatment of disease. In particular, the present disclosure is in the field of THR-β modulators and their use.

BACKGROUND OF THE DISCLOSURE

In parallel with the global increase in obesity, nonalcoholic fatty liver disease (NAFLD) is becoming the leading cause of chronic liver disease and liver transplantation worldwide [1,2]. NAFLD is believed to affect 30% of the adult population and 70-80% of individuals who are obese and diabetic. NAFLD is defined as excess liver fat accumulation greater than 5% induced by causes other than alcohol intake. NAFLD progresses to liver inflammation (nonalcoholic steatohepatitis, NASH) and fibrosis in a variable proportion of individuals, ultimately leading to liver failure and hepatocellular carcinoma (HCC) in susceptible individuals [3].

In the United States alone, NASH is the third most common indication for liver transplantation and is on a trajectory to become the most common [4]. The most important medical need in patients with NAFLD and NASH is an effective treatment to halt the progression and possibly reverse fibrosis, which is the main predictor of liver disease evolution [5,6].

Thyroid hormone (TH) is essential for normal development, growth and metabolism of all vertebrates. Its effects are mediated principally through triiodothyronine (T3), which acts as a ligand for the TH receptors (TRs, or THRs) β1, β2 and α1 [7]. In the absence of ligand, TR first binds as a heterodimer or homodimer on TH response elements (TRE) located in the promoter regions of target genes, where it interacts with corepressors. Upon ligand binding, the TR homodimers are dissociated in favor of heterodimer formation with the retinoid-X receptor (RXR), resulting in release of the corepressors and recruitment of coactivators. This new complex attracts a large number of proteins which engage the RNA polymerase II in the transcription of the targeted genes.

Two different genetic loci, denoted THRA and THRB, are responsible for encoding multiple interrelated TR isoforms that have distinct tissue distributions and biological functions. The two major isoforms with the broadest level of tissue expression are TRα1 and TRβ1 [8]. While TRα1 is expressed first during fetal development and is widely expressed in adult tissues, TRβ1 appears later in development and displays highest expression in the adult liver, kidney, and lung [9]. TRα1 is a key regulator of cardiac output, whereas TRβ1 helps in the control of metabolism in the liver. Importantly, the natural thyroid hormone T3 activates both TRα1 and TRβ1 without any significant selectivity.

Design of thyromimetic small molecule agents led to the identification of TR (or THR) agonists with varying levels of TRβ selectivity despite high structural similarity between the ligand-binding domains for TRβ and TRα. TRβ selectivity achieved by some of these compounds resulted in an improved therapeutic index for lipid lowering relative to cardiac effects such as heart rate, cardiac hypertrophy, and contractility [10-12].

Another strategy to avoid activation of TRα in cardiac tissue is to design prodrugs of phosphonate-containing TR agonists that are specifically converted to the active agonist in the liver but remain stable as an inactive prodrug in blood and extrahepatic tissues, including the heart [13]. TRα and TRβ agonists are also used in indications other than liver-related disorders, as has been known in the art. For example, TRβ selective agonists may be useful in the treatment of X-linked adrenoleukodystrophy [14, 15].

SUMMARY

Provided herein, in one aspect, are compounds of Formula I:

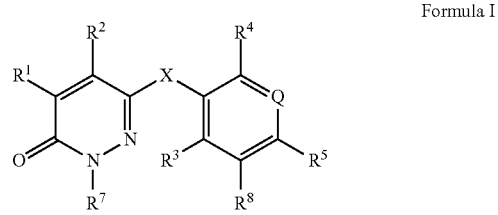

Formula I or a stereoisomer or a tautomer thereof, or a pharmaceutically acceptable salt thereof, wherein $R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens; or $R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens;

$R^3$ and $R^4$ are each independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;

$R^5$ is selected from:

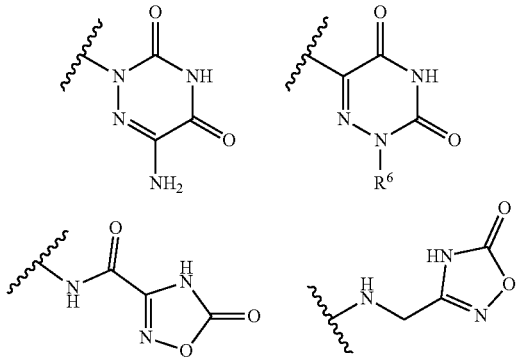

-continued

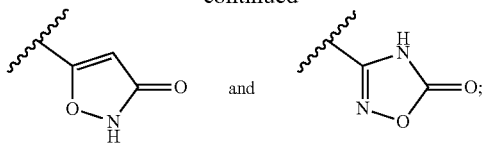

$R^6$ is H or $C_1$-$C_3$ alkyl;
$R^7$ is H or $C_1$-$C_3$ alkyl;
$R^8$ is selected from H, halogen, —CN, optionally substituted $C_1$-$C_3$ alkyl, and optionally substituted $C_1$-$C_2$ alkoxy; or
$R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;
Q is selected from N, CH, and CF; and
X is O or $CH_2$;
wherein when $R^1$ and $R^2$ together with the carbon atoms to which they are attached form a $C_6$ aromatic monocyclic ring, $R^5$ is selected from:

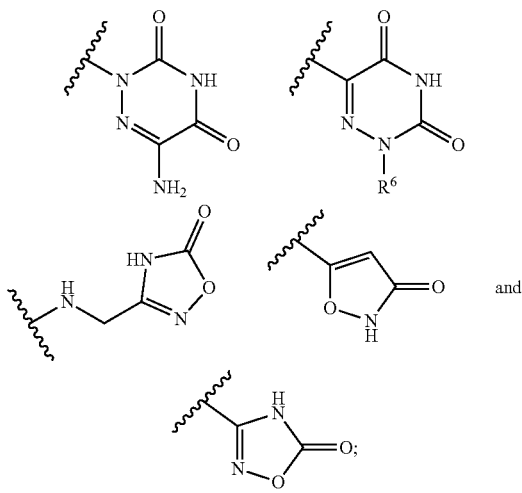

and
wherein 0 to 10 hydrogen atoms that are attached to one or more carbon atoms are replaced with deuterium atom(s).

In some embodiments, $R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens. In some embodiments, $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl. In some embodiments, $R^1$ and $R^2$ together with the carbon atoms to which they are attached form a $C_5$ monocyclic ring optionally substituted with 1 to 3 substituents independently selected from halogen and $C_1$-$C_6$ alkyl. In some embodiments, $R^1$ and $R^2$ together with the carbon atoms to which they are attached form a $C_6$ monocyclic ring optionally substituted with 1 to 3 substituents independently selected from halogen and $C_1$-$C_6$ alkyl. In some embodiments, $R^1$ and $R^2$ together with the carbon atoms to which they are attached form a $C_4$-$C_7$ monocyclic ring optionally substituted with $C_3$-$C_5$ cycloalkyl optionally substituted with 1-3 halogens. In some embodiments, $R^1$ and $R^2$ together with the carbon atoms to which they are attached form a $C_5$ monocyclic ring optionally substituted with $C_3$-$C_5$ cycloalkyl optionally substituted with 1-3 halogens. In some embodiments, $R^1$ and $R^2$ together with the carbon atoms to which they are attached form a $C_6$ monocyclic ring optionally substituted with $C_3$-$C_5$ cycloalkyl optionally substituted with 1-3 halogens. In some embodiments, the monocyclic ring is not aromatic. In some embodiments, $R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens. In some embodiments, $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from halogen and $C_1$-$C_3$ alkyl. In some embodiments, $R^3$ and $R^4$ are both halogen. In some embodiments, $R^3$ and $R^4$ are both $C_1$. In some embodiments, $R^3$ and $R^4$ are both methyl. In some embodiments, $R^8$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen. In some embodiments, $R^8$ is H. In some embodiments, $R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring. In some embodiments, $R^5$ is

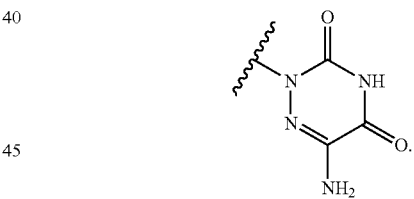

In some embodiments, X is $CH_2$. In some embodiments, X is O. In some embodiments, $R^7$ is H. In some embodiments, $R^7$ is $C_1$-$C_3$ alkyl. In some embodiments, Q is CH. In some embodiments, Q is N.

Provided herein, in another aspect, is a compound selected from the group consisting of:
(R)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;
(S)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(4-chloro-5-((7-methyl-1-oxo-2,5,6,7-tetrahydro-1H-cyclopenta[d]pyridazin-4-yl)oxy)bicyclo[4.2.0]octa-1,3,5-trien-2-yl)-1,2,4-triazine-3,5(2H,4H)-dione;
6-amino-2-(3,5-dichloro-4-((7-methyl-1-oxo-2,5,6,7-tetrahydro-1H-cyclopenta[d]pyridazin-4-yl)oxy)phenyl-2,6-d2)-1,2,4-triazine-3,5(2H,4H)-dione;

6-amino-2-(5-((7-cyclopropyl-1-oxo-2,5,6,7-tetrahydro-1H-cyclopenta[d]pyridazin-4-yl)oxy)-4-methylbicyclo[4.2.0]octa-1,3,5-trien-2-yl)-1,2,4-triazine-3,5(2H,4H)-dione;

6-amino-2-(3,5-dichloro-4-((7-ethyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7-cyclopropyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7-(3,3-difluorocyclobutyl)-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((4'-oxo-3',4',6',7'-tetrahydrospiro[cyclopentane-1,5'-cyclopenta[d]pyridazin]-1'-yl)oxy)phenyl)-1,2,4-triazine-3,5(2H,4H)-dione;

6-amino-2-(3,5-dichloro-4-((4-oxo-3,4,6,7-tetrahydrospiro[cyclopenta[d]pyridazine-5,1'-cyclopropan]-1-yl)oxy)phenyl)-1,2,4-triazine-3,5(2H,4H)-dione;

6-amino-2-(3,5-dichloro-4-((4'-oxo-3',4',6',7'-tetrahydrospiro[cyclobutane-1,5'-cyclopenta[d]pyridazin]-1'-yl)oxy)phenyl)-1,2,4-triazine-3,5(2H,4H)-dione;

6-amino-2-(3,5-dichloro-4-((4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-methyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-ethyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-cyclopropyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5,5-dimethyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5,5-diethyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-oxo-3,4-diazabicyclo[4.2.0]octa-1(6),2-dien-2-yl)oxy)phenyl)-1,2,4-triazine-3,5(2H,4H)-dione;

6-amino-2-(3,5-dichloro-4-((1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7,7-dimethyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7,7-diethyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((4-oxo-3,4,4b,5,5a,6-hexahydrocyclopropa[3,4]cyclopenta[1,2-d]pyridazin-1-yl)oxy)phenyl)-1,2,4-triazine-3,5(2H,4H)-dione;

6-amino-2-(3,5-dichloro-4-((5-methyl-4-oxo-3,4,5,6,7,8-hexahydro-5,8-ethanophthalazin-1-yl)oxy)phenyl)-1,2,4-triazine-3,5(2H,4H)-dione;

6-amino-2-(3,5-dichloro-4-((9-methyl-1-oxo-2,5,6,7,8,9-hexahydro-1H-cyclohepta[d]pyridazin-4-yl)oxy)phenyl)-1,2,4-triazine-3,5(2H,4H)-dione;

6-amino-2-(3,5-dichloro-4-((7-methyl-1-oxo-2,5,6,7-tetrahydro-1H-cyclopenta[d]pyridazin-4-yl)oxy)phenyl-2-d)-1,2,4-triazine-3,5(2H,4H)-dione;

6-amino-2-(3,5-dichloro-4-((7-cyclopropyl-1-oxo-2,5,6,7-tetrahydro-1H-cyclopenta[d]pyridazin-4-yl)oxy)phenyl-2-d)-1,2,4-triazine-3,5(2H,4H)-dione;

6-amino-2-(3,5-dichloro-2-fluoro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(4-chloro-6-methyl-5-((7-methyl-1-oxo-2,5,6,7-tetrahydro-1H-cyclopenta[d]pyridazin-4-yl)oxy)pyridin-2-yl)-1,2,4-triazine-3,5(2H,4H)-dione; and 6-amino-2-(3,5-dichloro-4-((4-oxo-3,4,5,6,7,8-hexahydro-5,8-methanophthalazin-1-yl)oxy)phenyl)-1,2,4-triazine-3,5(2H,4H)-dione;

or a stereoisomer or a tautomer thereof, or a pharmaceutically acceptable salt thereof.

Provided herein, in another aspect, is a pharmaceutical composition comprising a compound disclosed herein and at least one pharmaceutically acceptable excipient.

Provided herein, in another aspect, is a method of treating a disorder or disease in a subject in need thereof, the method comprising administering to the subject a therapeutically effective amount of a compound disclosed herein or a therapeutically effective amount of a pharmaceutical composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a use of a compound disclosed herein for the manufacture of a medicament for the treatment of a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a compound disclosed herein for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a composition disclosed herein for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a method of treating a thyroid hormone receptor related disorder in a patient, the method comprising the steps of identifying a patient in need of treatment for the thyroid hormone receptor related disorder, and administering to the patient, or contacting the patient with, a compound disclosed herein or a therapeutically effective amount of a pharmaceutical composition disclosed herein. In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Provided herein, in another aspect, is a method of selectively modulating the activity of a thyroid hormone receptor beta (THR-β) comprising contacting a compound disclosed herein with the thyroid hormone receptor. In some embodiments, the contacting is in vitro or ex vivo. In some embodiments, the contacting is in vivo.

Provided herein, in another aspect, is a compound disclosed herein for use in selectively modulating the activity of a thyroid hormone receptor beta (THR-β).

Provided herein, in another aspect, is a composition disclosed herein for use in selectively modulating the activity of a thyroid hormone receptor beta (THR-β).

DETAILED DESCRIPTION

Definitions

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In the definition of chemical substituents, each of $R_x$ and $R_y$ is independently hydrogen, alkyl, carbocyclic ring, heterocyclic ring, aryl, or heteroaryl, all of which, except hydrogen, are optionally substituted.

Unless otherwise indicated, the abbreviations "TR" and "THR" refer to thyroid hormone receptors.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methane-sulfonates, ethanesulfonates, p-toluenesulfonates and salicylates.

As used herein, "pharmaceutically acceptable ester" refers to an ester of a compound that does not cause significant irritation to a patient to which it is administered. The ester is metabolized in the body to result in the parent compound, e.g., the claimed compound. Accordingly, the ester does not abrogate the biological activity and properties of the compound. Pharmaceutical esters can be obtained by reaction of a compound disclosed herein with an alcohol. Methyl, ethyl, and isopropyl esters are some of the common esters to be prepared. Other esters suitable are well-known to those skilled in the art (see, for example Wuts, P. G. M., Greene's Protective Groups in Organic Synthesis, 5$^{th}$ Ed., John Wiley & Sons, New York, N.Y., 2014, which is incorporated herein by reference in its entirety).

Where the compounds disclosed herein have at least one chiral center, they may exist as a racemate or as individual enantiomers. It should be noted that all such isomers and mixtures thereof are included in the scope of the present disclosure. Thus, the illustration of a chiral center without a designation of R or S signifies that the scope of the disclosure includes the R isomer, the S isomer, the racemic mixture of the isomers, or mixtures where one isomer is present in greater abundance than the other.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides followed by chromatographic separation and removal of the chiral auxiliary.

Unless otherwise indicated, when a substituent is deemed to be "optionally substituted" it is meant that the substituent is a group that may be substituted with one or more (e.g., 1 or 2, or 1 to 3, or 1 to 4 or 1 to 5, or 1 to 6) group(s) individually and independently selected, without limitation, from alkyl, alkenyl, alkynyl, cycloalkyl, aryl, heteroaryl, heterocycloalkyl, hydroxy, alkoxy, aryloxy, mercapto, alkylthio, arylthio, cyano, halo, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, O-carboxy, is O-cyanato, thiocyanato, isothiocyanato, nitro, silyl, trihalomethanesulfonyl, and amino (e.g., —$NR_xR_y$), including mono- and di-substituted amino groups, and the protected derivatives thereof. The protecting groups that may form the protective derivatives of the above substituents are known to those of skill in the art and may be found in references such as Wuts, above.

As used herein, a "carbocyclic ring" is an aromatic or non-aromatic ring structure in which all the atoms in the ring are carbon atoms. As such, the ring structure may be fully saturated, fully unsaturated, or partially saturated. If any of the atoms in the ring is anything other than a carbon atom, then the ring is a "heterocyclic ring." Examples of atoms that are within a ring include sulfur, oxygen, and nitrogen. A carbocyclic ring or a heterocyclic ring may be polycyclic, e.g., a fused ring system, a spirocyclic ring system, or a bridged ring system. These polycyclic rings include, for example, adamantyl, norbornyl (i.e., bicyclo[2.2.1]heptanyl), norbornenyl, decalinyl, 7,7-dimethyl-bicyclo[2.2.1] heptanyl, and the like. Additional non-limiting examples include bicyclic rings such as but not limited to:

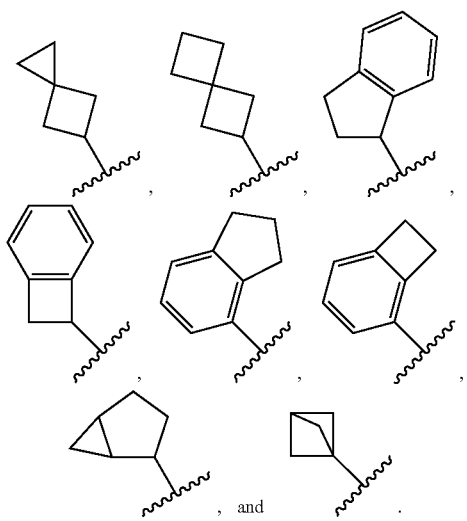

As used herein, "aryl" refers to a carbocyclic (all carbon) ring that has a fully delocalized pi-electron system. The "aryl" group can be made up of two or more fused rings (rings that share two adjacent carbon atoms). When the aryl is a fused ring system, then the ring that is connected to the rest of the molecule has a fully delocalized pi-electron system. The other ring(s) in the fused ring system may or may not have a fully delocalized pi-electron system. Further, the other ring(s) may or may not contain one or more heteroatoms (e.g., O, N, or S). Examples of aryl groups include, without limitation, the radicals of benzene, naphthalene and azulene. Additional non-limiting examples include:

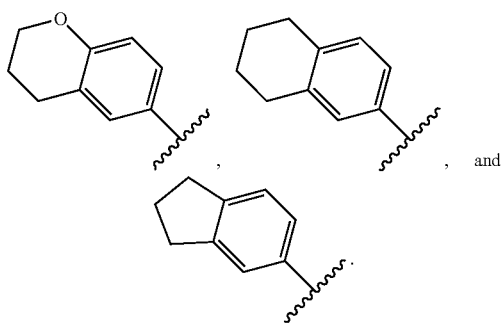

As used herein, "heteroaryl" refers to a ring that has a fully delocalized pi-electron system and contains one or more heteroatoms selected from the group consisting of nitrogen, oxygen, and sulfur in the ring. The "heteroaryl" group can be made up of two or more fused rings (rings that share two adjacent carbon atoms). When the heteroaryl is a fused ring system, then the ring that is connected to the rest of the molecule has a fully delocalized pi-electron system. The other ring(s) in the fused ring system may or may not have a fully delocalized pi-electron system. Examples of heteroaryl rings include, without limitation, furan, thiophene, phthalazinone, pyrrole, oxazole, thiazole, imidazole, pyrazole, isoxazole, isothiazole, triazole, thiadiazole, pyridine, pyridazine, pyrimidine, pyrazine and triazine.

Wherever "hetero" is used it is intended to mean a group as specified, such as an alkyl or an aryl group, where at least one carbon atom has been replaced with a heteroatom selected from nitrogen, oxygen and sulfur.

As used herein, "alkyl" refers to a straight or branched chain fully saturated (no double or triple bonds) hydrocarbon group. An alkyl group of the presently disclosed compounds may comprise from 1 to 20 carbon atoms. An alkyl group herein may also be of medium size having 1 to 10 carbon atoms. An alkyl group herein may also be a lower alkyl having 1 to 5 carbon atoms or 1 to 6 carbon atoms. Examples of alkyl groups include, without limitation, methyl, ethyl, n-propyl, isopropyl, n-butyl, i-butyl, sec-butyl, t-butyl, amyl, t-amyl, hexyl, heptyl, octyl, nonyl, decyl, undecyl and dodecyl.

An alkyl group of the presently disclosed compounds may be substituted or unsubstituted. When substituted, the substituent group(s) can be one or more group(s) independently selected from cycloalkyl, aryl, heteroaryl, heterocycloalkyl, hydroxy, protected hydroxy, alkoxy, aryloxy, mercapto, alkylthio, arylthio, cyano, halogen, carbonyl, thiocarbonyl, O-carbamoyl, N-carbamoyl, O-thiocarbamoyl, N-thiocarbamoyl, C-amido, N-amido, S-sulfonamido, N-sulfonamido, C-carboxy, protected C-carboxy, O-carboxy, isocyanato, thiocyanato, isothiocyanato, nitro, silyl, trihalomethanesulfonyl, amino (e.g., $-NR_xR_y$) and protected amino.

As used herein, "alkenyl" refers to an alkyl group that contains in the straight or branched hydrocarbon chain one or more double bonds. An alkenyl group of the presently disclosed compounds may be unsubstituted or substituted. When substituted, the substituent(s) may be selected from the same groups disclosed above regarding alkyl group substitution, or with regard to optional substitution.

As used herein, "alkynyl" refers to an alkyl group that contains in the straight or branched hydrocarbon chain one or more triple bonds. An alkynyl group of the presently disclosed compounds may be unsubstituted or substituted. When substituted, the substituent(s) may be selected from the same groups disclosed above regarding alkyl group substitution, or with regard to optional substitution.

As used herein, "acyl" refers to an "$R_xC(=O)-$" group.

As used herein, "cycloalkyl" refers to a completely saturated (no double bonds) hydrocarbon ring. In some embodiments, cycloalkyl refers to a hydrocarbon ring containing no double bonds or one or more double bonds provided that they do not form a fully delocalized pi-electron system in the ring. Cycloalkyl groups of the presently disclosed compounds may range from $C_3$ to $C_8$. A cycloalkyl group may be unsubstituted or substituted. If substituted, the substituent(s) may be selected from those indicated above regarding substitution of an alkyl group. The "cycloalkyl" group can be made up of two or more fused rings (rings that share two adjacent carbon atoms). When the cycloalkyl is a fused ring system, then the ring that is connected to the rest of the molecule is a cycloalkyl as defined above. The other ring(s) in the fused ring system may be a cycloalkyl, a cycloalkenyl, an aryl, a heteroaryl, or a heterocycloalkyl.

As used herein, "cycloalkenyl" refers to a cycloalkyl group that contains one or more double bonds in the ring although, if there is more than one, they cannot form a fully delocalized pi-electron system in the ring (otherwise the group would be "aryl," as defined herein). A cycloalkenyl group of the presently disclosed compounds may unsubstituted or substituted. When substituted, the substituent(s) may be selected from the same groups disclosed above regarding alkyl group substitution. The "cycloalkenyl" group can be made up of two or more fused rings (rings that share two adjacent carbon atoms). When the cycloalkenyl is a fused ring system, then the ring that is connected to the rest of the molecule is a cycloalkenyl as defined above. The other ring(s) in the fused ring system may be a cycloalkyl, a cycloalkenyl, an aryl, a heteroaryl, or a heterocycloalkyl.

The term "alkylene" refers to an alkyl group, as defined herein, which is a biradical and is connected to two other moieties. Thus, methylene (—CH$_2$—), ethylene (—CH$_2$CH$_2$—), propylene (—CH$_2$CH$_2$CH$_2$—), isopropylene (IUPAC: (methyl)ethylene) (—CH$_2$—CH(CH$_3$)—), and isobutylene (IUPAC: 2-(methyl)propylene) (—CH$_2$—CH(CH$_3$)—CH$_2$—) are examples, without limitation, of an alkylene group. Similarly, the term "cycloalkylene" refers to a cycloalkyl group, as defined here, which binds in an analogous way to two other moieties. If the alkyl and cycloalkyl groups contain unsaturated carbons, the terms "alkenylene" and "cycloalkenylene" are used.

As used herein, "heterocycloalkyl," "heteroalicyclic," or "heteroali-cyclyl" refers to a ring having in the ring system one or more heteroatoms independently selected from nitrogen, oxygen and sulfur. The ring may also contain one or more double bonds provided that they do not form a fully delocalized pi-electron system in the rings. The ring defined herein can be a stable 3- to 18-membered ring that consists of carbon atoms and from one to five heteroatoms selected from the group consisting of nitrogen, oxygen, and sulfur. Heterocycloalkyl, groups of the presently disclosed compounds may be unsubstituted or substituted. When substituted, the substituent(s) may be one or more groups independently selected from the group consisting of halogen, hydroxy, protected hydroxy, cyano, nitro, alkyl, alkoxy, acyl, acyloxy, carboxy, protected carboxy, amino, protected amino, carboxamide, protected carboxamide, alkylsulfonamido and trifluoromethane-sulfonamido. The "heterocycloalkyl" group can be made up of two or more fused rings (rings that share two adjacent carbon atoms). When the heterocycloalkyl is a fused ring system, then the ring that is connected to the rest of the molecule is a heterocycloalkyl as defined above. The other ring(s) in the fused ring system may be a cycloalkyl, a cycloalkenyl, an aryl, a heteroaryl, or a heterocycloalkyl.

As used herein, "aralkyl" refers to an alkylene substituted with an aryl group.

As used herein, "carbocyclic alkyl" or "(carbocyclic) alkyl" refers to an alkylene substituted with a carbocyclic group.

As used herein, "heterocyclicalkyl" or (heterocyclic)alkyl" refers to an alkylene substituted with a heterocyclic group. Similarly, "(heterocycloalkyl)alkyl" refers to an alkylene substituted with a heterocycloalkyl group.

As used herein, "heteroarylalkyl" or "(heteroaryl)alkyl" refers to an alkylene substituted with a heteroaryl group.

An "O-carboxy" group refers to a "R$_x$C(=O)O—" group.
A "C-carboxy" group refers to a "—C(=O)OR$_x$" group.
An "acetyl" group refers to a CH$_3$C(=O)— group.
A "C-amido" group refers to a "—C(=O)NR$_x$R$_y$" group.
An "N-amido" group refers to a "R$_y$C(=O)NR$_x$—" group.

The term "perhaloalkyl" refers to an alkyl group in which all the hydrogen atoms are replaced by halogen atoms.

Any unsubstituted or monosubstituted amine group on a compound herein can be converted to an amide, any hydroxy group can be converted to an ester and any carboxyl group can be converted to either an amide or ester using techniques well-known to those skilled in the art (see, for example Wuts, above).

It is understood that, in any compound of the presently disclosed compounds having one or more chiral centers, if an absolute stereochemistry is not expressly indicated, then each center may independently be R or S or a mixture thereof. In addition, it is understood that, in any compound of the presently disclosed compounds having one or more double bond(s) generating geometrical isomers that can be defined as E or Z each double bond may independently be E or Z, or a mixture thereof.

It is understood that the disclosure of a compound herein inherently includes the disclosure of a tautomer thereof, if applicable. For instance, the disclosure of:

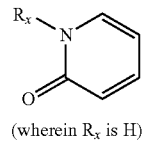

(wherein R$_x$ is H)

also includes the disclosure of:

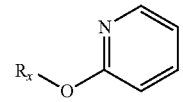

and vice versa, even if only one of the two structures is disclosed.

Throughout the present disclosure, when a compound is illustrated or named, it is understood that the isotopically enriched analogs of the compound are also contemplated. For example, a compound may have a deuterium incorporated instead of a hydrogen, or a carbon-13 instead of carbon with natural isotopic distribution. The isotopic enrichment may be in one location on the compound, i.e., only one hydrogen is replaced by a deuterium, or in more than one location. The present disclosure also encompasses compounds where all the similar atoms are replaced by their less common isotope, for example, a perdeutero compound where all the hydrogen atoms are replaced by a deuterium. The isotopically enriched compounds are useful when obtaining NMR spectra or when making use of an isotope effect in managing the kinetics of the reaction the compound undergoing.

The term "pharmaceutical composition" refers to a mixture of one or more compounds disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example, dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

In certain embodiments, the same substance can act as a carrier, diluent, or excipient, or have any of the two roles, or have all three roles. Thus, a single additive to the pharmaceutical composition can have multiple functions.

The term "pharmaceutically acceptable" defines a carrier or diluent that does not abrogate the biological activity and properties of the compound.

Compounds

In one aspect, provided herein are compounds of Formula I:

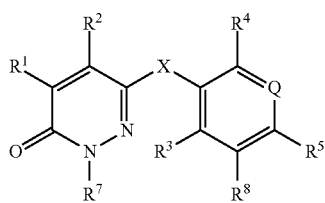

Formula I or a stereoisomer or a tautomer thereof, or a pharmaceutically acceptable salt thereof, wherein
  $R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens; or
  $R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens; $R^3$ and $R^4$ are each independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;
  $R^5$ is selected from:

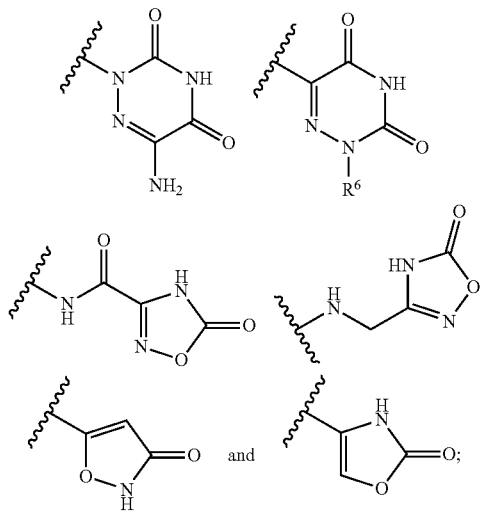

$R^6$ is H or $C_1$-$C_3$ alkyl;
  $R^7$ is H or $C_1$-$C_3$ alkyl optionally substituted with 1-5 halogens;
  $R^8$ is selected from H, halogen, —CN, optionally substituted $C_1$-$C_3$ alkyl, and optionally substituted $C_1$-$C_2$ alkoxy; or
  $R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;
  Q is selected from N, CH, and CF; and
  X is O or $CH_2$;
  wherein when $R^1$ and $R^2$ together with the carbon atoms to which they are attached form a $C_6$ aromatic monocyclic ring, $R^5$ is selected from:

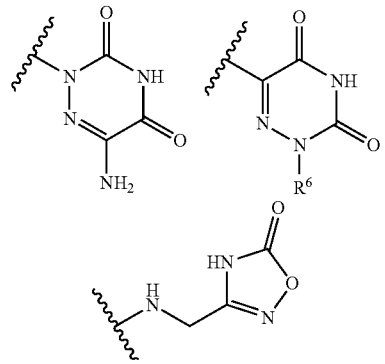

wherein 0 to 10 hydrogen atoms that are attached to one or more carbon atoms are replaced with deuterium atom(s).

In some embodiments, $R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens. In some embodiments, $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl. In some embodiments, $R^1$ and $R^2$ together with the carbon atoms to which they are attached form a $C_5$ monocyclic ring optionally substituted with 1 to 3 substituents independently selected from halogen and $C_1$-$C_6$ alkyl. In some embodiments, $R^1$ and $R^2$ together with the carbon atoms to which they are attached form a $C_6$ monocyclic ring optionally substituted with 1 to 3 substituents independently selected from halogen and $C_1$-$C_6$ alkyl. In some embodiments, $R^1$ and $R^2$ together with the carbon atoms to which they are attached form a $C_4$-$C_7$ monocyclic ring optionally substituted with $C_3$-$C_5$ cycloalkyl optionally substituted with 1-3 halogens. In some embodiments, $R^1$ and $R^2$ together with the carbon atoms to which they are attached form a $C_5$ monocyclic ring optionally substituted with $C_3$-$C_5$ cycloalkyl optionally substituted with 1-3 halogens. In some embodiments, $R^1$ and $R^2$ together with the carbon atoms to which they are attached form a $C_6$ monocyclic ring optionally substituted with $C_3$-$C_5$ cycloalkyl optionally substituted with 1-3 halogens. In some embodiments, the monocyclic ring is not aromatic.

In some embodiments, $R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens. In some embodiments, $R^1$ and $R^2$ together with the carbon atoms to which they are attached form a polycyclic ring optionally substituted with 1 to 3 substituents independently selected from $C_1$-$C_6$ alkyl. In some embodiments, the polycyclic ring is a spirocyclic ring system. In some embodiments, the polycyclic ring is a fused ring system. In some embodiments, the polycyclic ring is a bridged ring system.

In some embodiments, $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from $C_1$; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl. In some embodiments, $R^3$ and $R^4$ are each independently selected from halogen and $C_1$-$C_3$ alkyl. In some embodiments, $R^3$ and $R^4$ are both halogen. In some embodiments, $R^3$ and $R^4$ are both $C_1$. In some embodiments, $R^3$ and $R^4$ are both methyl.

In some embodiments, $R^5$ is selected from:

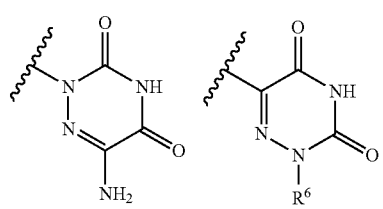

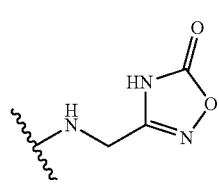

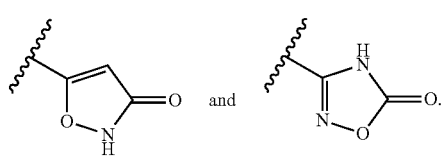 and

In some embodiments, $R^5$ is

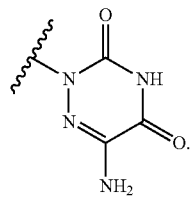

In some embodiments, $R^5$ is

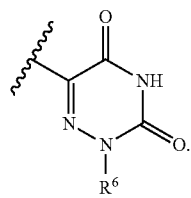

In some embodiments, $R^5$ is

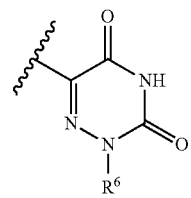

and $R^6$ is H. In some embodiments, $R^5$ is

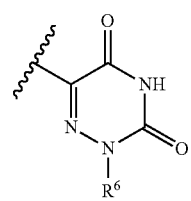

and $R^6$ is $C_1$-$C_3$ alkyl.

In some embodiments, $R^5$ is

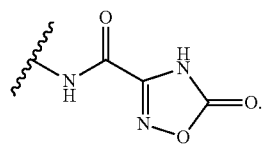 [SMILES: *NC(=O)c1noc(=O)[nH]1]

In some embodiments, $R^5$ is

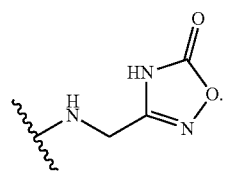 [SMILES: *NCc1noc(=O)[nH]1]

In some embodiments, $R^5$ is

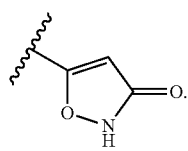 [SMILES: *c1cc(=O)[nH]o1]

In some embodiments, $R^5$ is

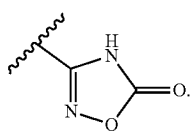 [SMILES: *c1noc(=O)[nH]1]

In some embodiments, Q is CH, CD, or CF. In some embodiments, Q is CH. In some embodiments, Q is CD. In some embodiments, Q is CF. In some embodiments, Q is N.

In some embodiments, X is $CH_2$. In some embodiments, X is O.

In some embodiments, $R^7$ is H. In some embodiments, $R^7$ is $C_1$-$C_3$ alkyl.

In some embodiments, $R^8$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen. In some embodiments, $R^8$ is hydrogen or $C_1$-$C_3$ alkyl. In some embodiments, $R^8$ is hydrogen.

In some embodiments, $R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring. In some embodiments, $R^3$ and $R^8$ together with the carbon atoms to which they are attached form a 4-, 5-, or 6-membered partially unsaturated carbocyclic ring. In some embodiments, $R^3$ and $R^8$ together with the carbon atoms to which they are attached form a 4-, 5-, or 6-membered partially unsaturated heterocyclic ring. In some embodiments, $R^3$ and $R^8$ together with the carbon atoms to which they are attached form a $C_6$-$C_{10}$ aryl ring. In some embodiments, $R^3$ and $R^8$ together with the carbon atoms to which they are attached form a 5- or 6-membered heteroaryl ring.

In some embodiments, the compound of Formula I has the chemical structure of:

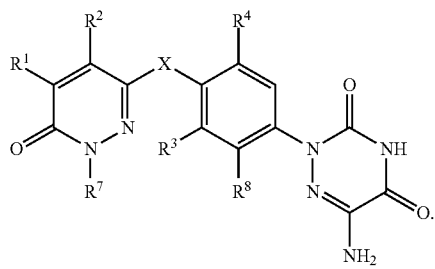

In some embodiments, the compound of Formula I has the chemical structure of:

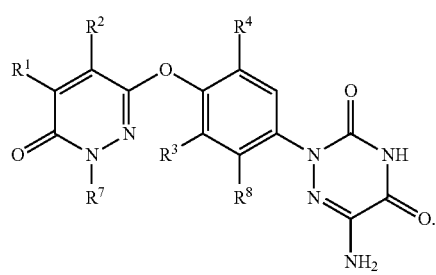

In some embodiments, the compound of Formula I has the chemical structure of:

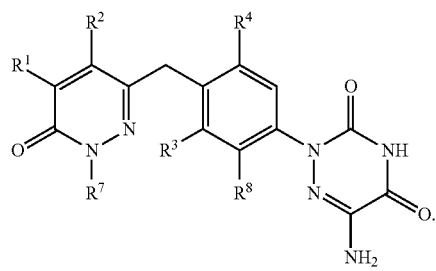

In some embodiments, the compound of Formula I has the chemical structure of:

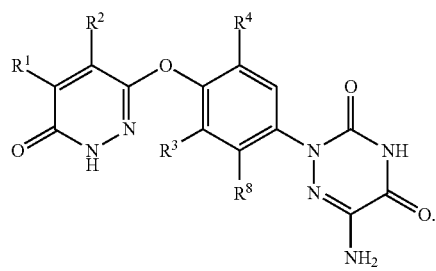

In some embodiments, the compound of Formula I has the chemical structure of:

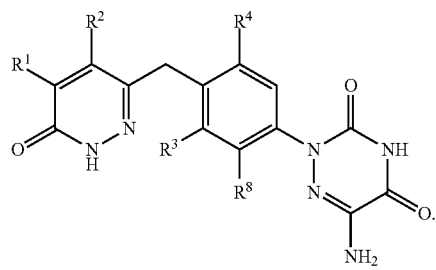

In some embodiments, the compound of Formula I has the chemical structure of:

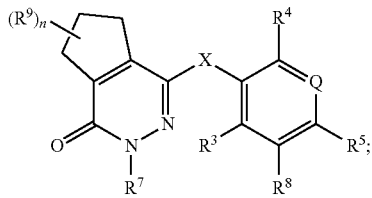

wherein each $R^9$ is independently selected from halogen, $C_1$-$C_6$ alkyl, and $C_3$-$C_5$ cycloalkyl optionally substituted with 1-3 halogens; and n is 0, 1, 2, 3, or 4.

In some embodiments, the compound of Formula I has the chemical structure of:

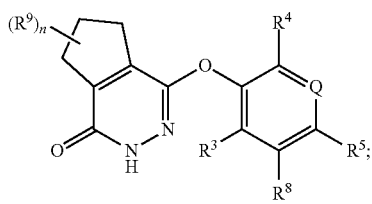

wherein each $R^9$ is independently selected from halogen, $C_1$-$C_6$ alkyl, and $C_3$-$C_5$ cycloalkyl optionally substituted with 1-3 halogens; and n is 0, 1, 2, 3, or 4.

In some embodiments, the compound of Formula I has the chemical structure of:

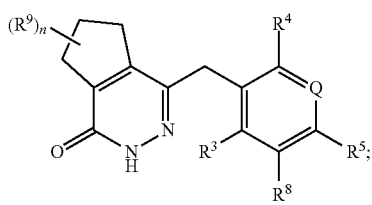

wherein each $R^9$ is independently selected from halogen, $C_1$-$C_6$ alkyl, and $C_3$-$C_5$ cycloalkyl optionally substituted with 1-3 halogens; and n is 0, 1, 2, 3, or 4.

In some embodiments, the compound of Formula I has the chemical structure of:

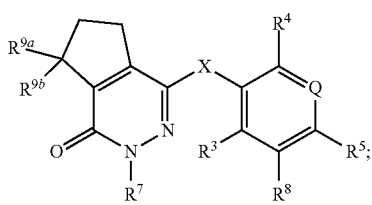

wherein $R^{9a}$ and $R^{9b}$ are each independently selected from H, halogen, $C_1$-$C_6$ alkyl, and $C_3$-$C_5$ cycloalkyl optionally substituted with 1-3 halogens; or $R^{9a}$ and $R^{9b}$ together with the carbon atom to which they are attached form a $C_3$-$C_6$ monocyclic ring optionally substituted with 1 to 3 substituents independently selected from halogen and $C_1$-$C_6$ alkyl.

In some embodiments, the compound of Formula I has the chemical structure of:

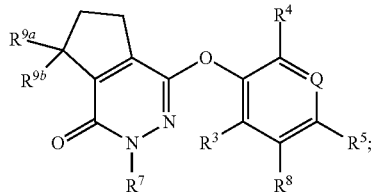

wherein $R^{9a}$ and $R^{9b}$ are each independently selected from H, halogen, $C_1$-$C_6$ alkyl, and $C_3$-$C_5$ cycloalkyl optionally substituted with 1-3 halogens; or $R^{9a}$ and $R^{9b}$ together with the carbon atom to which they are attached form a $C_3$-$C_6$ monocyclic ring optionally substituted with 1 to 3 substituents independently selected from halogen and $C_1$-$C_6$ alkyl.

In some embodiments, the compound of Formula I has the chemical structure of:

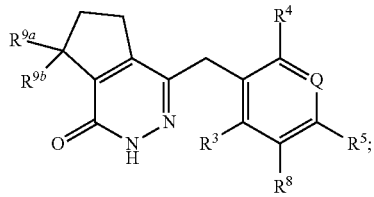

wherein $R^{9a}$ and $R^{9b}$ are each independently selected from H, halogen, $C_1$-$C_6$ alkyl, and $C_3$-$C_5$ cycloalkyl optionally substituted with 1-3 halogens; or $R^{9a}$ and $R^{9b}$ together with the carbon atom to which they are attached form a $C_3$-$C_6$ monocyclic ring optionally substituted with 1 to 3 substituents independently selected from halogen and $C_1$-$C_6$ alkyl.

In some embodiments, the compound of Formula I has the chemical structure of:

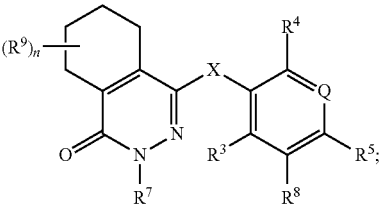

wherein each $R^9$ is independently selected from halogen, $C_1$-$C_6$ alkyl, and $C_3$-$C_5$ cycloalkyl optionally substituted with 1-3 halogens; and n is 0, 1, 2, 3, or 4.

In some embodiments, the compound of Formula I has the chemical structure of:

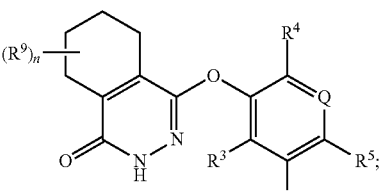

wherein each $R^9$ is independently selected from halogen, $C_1$-$C_6$ alkyl, and $C_3$-$C_5$ cycloalkyl optionally substituted with 1-3 halogens; and n is 0, 1, 2, 3, or 4.

In some embodiments, the compound of Formula I has the chemical structure of:

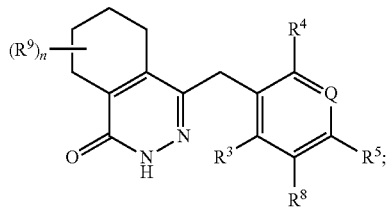

wherein each $R^9$ is independently selected from halogen, $C_1$-$C_6$ alkyl, and $C_3$-$C_5$ cycloalkyl optionally substituted with 1-3 halogens; and n is 0, 1, 2, 3, or 4.

In some embodiments, the compound of Formula I has the chemical structure of:

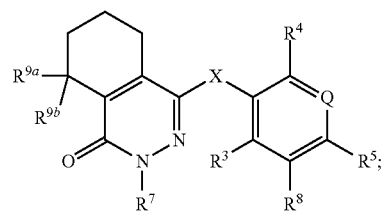

wherein $R^{9a}$ and $R^{9b}$ are each independently selected from H, halogen, $C_1$-$C_6$ alkyl, and $C_3$-$C_5$ cycloalkyl optionally substituted with 1-3 halogens; or $R^{9a}$ and $R^{9b}$ together with the carbon atom to which they are attached form a $C_3$-$C_6$ monocyclic ring optionally substituted with 1 to 3 substituents independently selected from halogen and $C_1$-$C_6$ alkyl.

In some embodiments, the compound of Formula I has the chemical structure of:

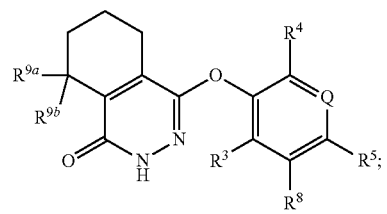

wherein $R^{9a}$ and $R^{9b}$ are each independently selected from H, halogen, $C_1$-$C_6$ alkyl, and $C_3$-$C_5$ cycloalkyl optionally substituted with 1-3 halogens; or $R^{9a}$ and $R^{9b}$ together with the carbon atom to which they are attached form a $C_3$-$C_6$ monocyclic ring optionally substituted with 1 to 3 substituents independently selected from halogen and $C_1$-$C_6$ alkyl.

In some embodiments, the compound of Formula I has the chemical structure of:

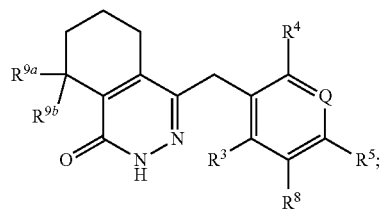

wherein $R^{9a}$ and $R^{9b}$ are each independently selected from H, halogen, $C_1$-$C_6$ alkyl, and $C_3$-$C_5$ cycloalkyl optionally substituted with 1-3 halogens; or $R^{9a}$ and $R^{9b}$ together with the carbon atom to which they are attached form a $C_3$-$C_6$ monocyclic ring optionally substituted with 1 to 3 substituents independently selected from halogen and $C_1$-$C_6$ alkyl.

In some embodiments, n is 0. In some embodiments, n is 1. In some embodiments, n is 2. In some embodiments, n is 3. In some embodiments, n is 4.

In some embodiments, $R^9$ is selected from halogen, $C_1$-$C_6$ alkyl, and $C_3$-$C_5$ cycloalkyl optionally substituted with 1-3 halogens. In some embodiments, $R^9$ is halogen. In some embodiments, $R^9$ is $C_1$-$C_6$ alkyl. In some embodiments, $R^9$ is methyl. In some embodiments, $R^9$ is ethyl. In some embodiments, $R^9$ is $C_3$-$C_5$ cycloalkyl optionally substituted with 1-3 halogens. In some embodiments, $R^9$ is cyclopropyl optionally substituted with 1-3 halogens. In some embodiments, $R^9$ is cyclopropyl substituted with 2 fluorines. In some embodiments, $R^9$ is cyclobutyl optionally substituted with 1-3 halogens. In some embodiments, $R^9$ is cyclobutyl substituted with two fluorines.

In some embodiments, $R^{9a}$ is selected from halogen, $C_1$-$C_6$ alkyl, and $C_3$-$C_5$ cycloalkyl optionally substituted with 1-3 halogens. In some embodiments, $R^{9a}$ is halogen. In some embodiments, $R^{9a}$ is $C_1$-$C_6$ alkyl. In some embodiments, $R^{9a}$ is methyl. In some embodiments, $R^{9a}$ is ethyl. In some embodiments, $R^{9a}$ is $C_3$-$C_5$ cycloalkyl optionally substituted with 1-3 halogens. In some embodiments, $R^{9a}$ is cyclopropyl optionally substituted with 1-3 halogens. In some embodiments, $R^{9a}$ is cyclopropyl substituted with 2 fluorines. In some embodiments, $R^{9a}$ is cyclobutyl optionally substituted with 1-3 halogens. In some embodiments, $R^{9a}$ is cyclobutyl substituted with two fluorines. In some embodiments, $R^{9b}$ is selected from halogen, $C_1$-$C_6$ alkyl, and $C_3$-$C_5$ cycloalkyl optionally substituted with 1-3 halogens. In some embodiments, $R^{9b}$ is halogen. In some embodiments, $R^{9b}$ is $C_1$-$C_6$ alkyl. In some embodiments, $R^{9b}$ is methyl. In some embodiments, $R^{9b}$ is ethyl. In some embodiments, $R^{9b}$ is $C_3$-$C_5$ cycloalkyl optionally substituted with 1-3 halogens. In some embodiments, $R^{9b}$ is cyclopropyl optionally substituted with 1-3 halogens. In some embodiments, $R^{9b}$ is cyclopropyl substituted with 2 fluorines. In some embodiments, $R^{9b}$ is cyclobutyl optionally substituted with 1-3 halogens. In some embodiments, $R^{9b}$ is cyclobutyl substituted with two fluorines.

In some embodiments, $R^{9a}$ and $R^{9b}$ together with the carbon atom to which they are attached form a $C_3$-$C_6$ monocyclic ring optionally substituted with 1 to 3 substituents independently selected from halogen and $C_1$-$C_6$ alkyl. In some embodiments, $R^{9a}$ and $R^{9b}$ together with the carbon atom to which they are attached form a $C_3$ monocyclic ring optionally substituted with 1 to 3 substituents independently selected from halogen and $C_1$-$C_6$ alkyl. In some embodiments, $R^{9a}$ and $R^{9b}$ together with the carbon atom to which they are attached form a $C_4$ monocyclic ring optionally substituted with 1 to 3 substituents independently selected from halogen and $C_1$-$C_6$ alkyl. In some embodiments, $R^{9a}$ and $R^{9b}$ together with the carbon atom to which they are attached form a $C_5$ monocyclic ring optionally substituted with 1 to 3 substituents independently selected from halogen and $C_1$-$C_6$ alkyl. In some embodiments, $R^{9a}$ and $R^{9b}$ together with the carbon atom to which they are attached form a $C_6$ monocyclic ring optionally substituted with 1 to 3 substituents independently selected from halogen and $C_1$-$C_6$ alkyl.

In another aspect, disclosed herein is a compound selected from the group consisting of:

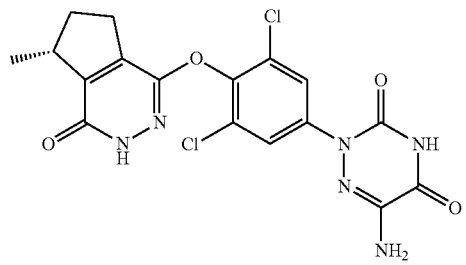 [SMILES: C[C@@H]1CCc2c(Oc3c(Cl)cc(-n4nc(N)c(=O)[nH]c4=O)cc3Cl)n[nH]c(=O)c21]

(R)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

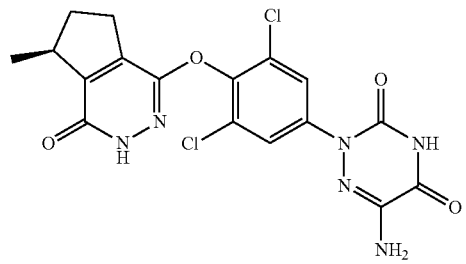 [SMILES: C[C@H]1CCc2c(Oc3c(Cl)cc(-n4nc(N)c(=O)[nH]c4=O)cc3Cl)n[nH]c(=O)c21]

(S)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

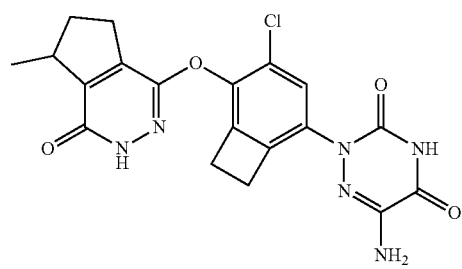 [SMILES: CC1CCc2c(Oc3c(Cl)cc(-n4nc(N)c(=O)[nH]c4=O)c4c3CC4)n[nH]c(=O)c21]

6-amino-2-(4-chloro-5-((7-methyl-1-oxo-2,5,6,7-tetrahydro-1H-cyclopenta[d]pyridazin-4-yl)oxy)bicyclo[4.2.0]octa-1,3,5-trien-2-yl)-1,2,4-triazine-3,5(2H,4H)-dione;

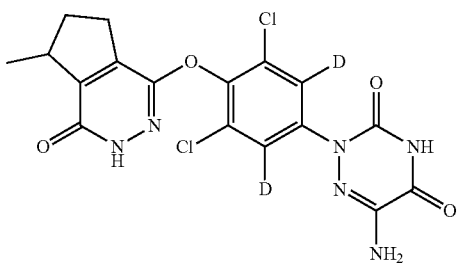 [SMILES: [2H]c1c(Cl)c(Oc2n[nH]c(=O)c3c2CCC3C)c(Cl)c([2H])c1-n1nc(N)c(=O)[nH]c1=O]

6-amino-2-(3,5-dichloro-4-((7-methyl-1-oxo-2,5,6,7-tetrahydro-1H-cyclopenta[d]pyridazin-4-yl)oxy)phenyl-2,6-d2)-1,2,4-triazine-3,5(2H,4H)-dione;

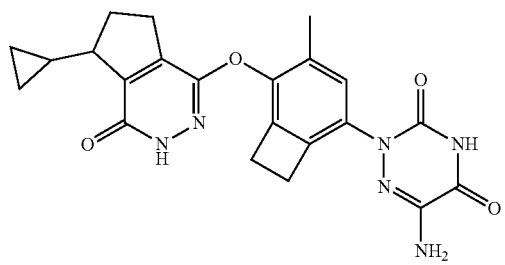 [SMILES: Cc1cc(-n2nc(N)c(=O)[nH]c2=O)c2c(c1Oc1n[nH]c(=O)c3c1CCC3C1CC1)CC2]

6-amino-2-(5-((7-cyclopropyl-1-oxo-2,5,6,7-tetrahydro-1H-cyclopenta[d]pyridazin-4-yl)oxy)-4-methylbicyclo[4.2.0]octa-1,3,5-trien-2-yl)-1,2,4-triazine-3,5(2H,4H)-dione;

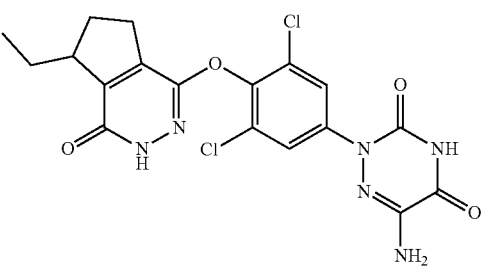 [SMILES: CCC1CCc2c(Oc3c(Cl)cc(-n4nc(N)c(=O)[nH]c4=O)cc3Cl)n[nH]c(=O)c21]

6-amino-2-(3,5-dichloro-4-((7-ethyl-1-oxo-2,5,6,7-tetrahydro-1H-cyclopenta[d]pyridazin-4-yl)oxy)phenyl)-1,2,4-triazine-3,5(2H,4H)-dione;

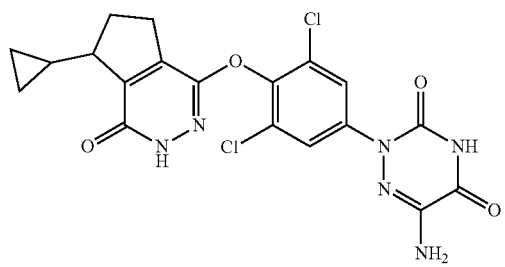 [SMILES: Nc1nn(-c2cc(Cl)c(Oc3n[nH]c(=O)c4c3CCC4C3CC3)c(Cl)c2)c(=O)[nH]c1=O]

6-amino-2-(3,5-dichloro-4-((7-cyclopropyl-1-oxo-2,5,6,7-tetrahydro-1H-cyclopenta[d]pyridazin-4-yl)oxy)phenyl)-1,2,4-triazine-3,5(2H,4H)-dione;

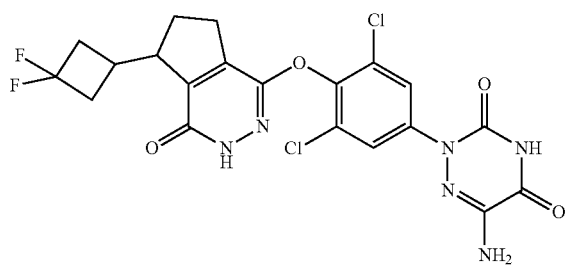 [SMILES: Nc1nn(-c2cc(Cl)c(Oc3n[nH]c(=O)c4c3CCC4C3CC(F)(F)C3)c(Cl)c2)c(=O)[nH]c1=O]

6-amino-2-(3,5-dichloro-4-((7-(3,3-difluorocyclobutyl)-1-oxo-2,5,6,7-tetrahydro-1H-cyclopenta[d]pyridazin-4-yl)oxy)phenyl)-1,2,4-triazine-3,5(2H,4H)-dione;

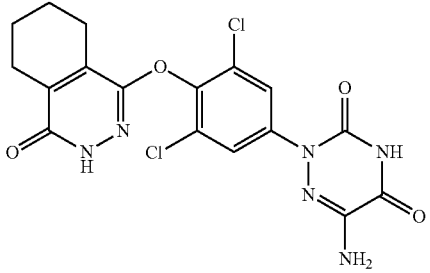

6-amino-2-(3,5-dichloro-4-((4-oxo-3,4,5,6,7,8-hexahydrophthalazin-1-yl)oxy)phenyl)-1,2,4-triazine-3,5(2H,4H)-dione;

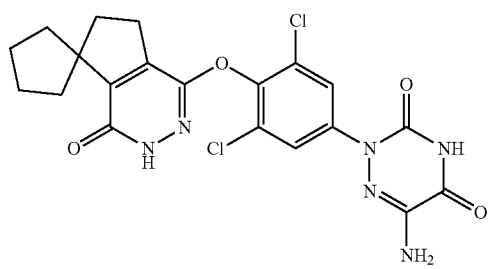 [SMILES: Nc1nn(-c2cc(Cl)c(Oc3n[nH]c(=O)c4c3CCC43CCCC3)c(Cl)c2)c(=O)[nH]c1=O]

6-amino-2-(3,5-dichloro-4-((4'-oxo-3',4',6',7'-tetrahydrospiro[cyclopentane-1,5'-cyclopenta[d]pyridazin]-1'-yl)oxy)phenyl)-1,2,4-triazine-3,5(2H,4H)-dione;

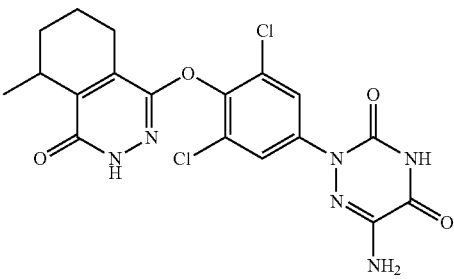

6-amino-2-(3,5-dichloro-4-((5-methyl-4-oxo-3,4,5,6,7,8-hexahydrophthalazin-1-yl)oxy)phenyl)-1,2,4-triazine-3,5(2H,4H)-dione;

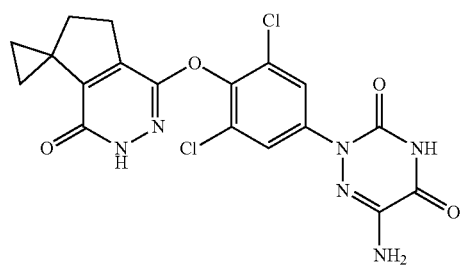

6-amino-2-(3,5-dichloro-4-((4-oxo-3,4,6,7-tetrahydrospiro[cyclopenta[d]pyridazine-5,1'-cyclopropan]-1-yl)oxy)phenyl)-1,2,4-triazine-3,5(2H,4H)-dione;

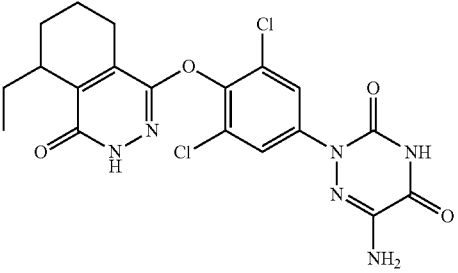

6-amino-2-(3,5-dichloro-4-((5-ethyl-4-oxo-3,4,5,6,7,8-hexahydrophthalazin-1-yl)oxy)phenyl)-1,2,4-triazine-3,5(2H,4H)-dione;

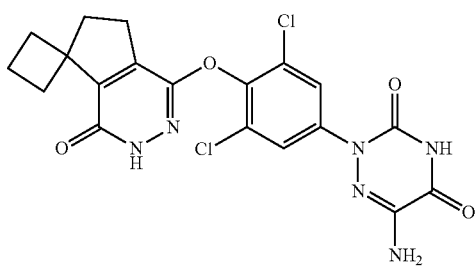 [SMILES: Nc1nn(-c2cc(Cl)c(Oc3n[nH]c(=O)c4c3CCC43CCC3)c(Cl)c2)c(=O)[nH]c1=O]

6-amino-2-(3,5-dichloro-4-((4'-oxo-3',4',6',7'-tetrahydrospiro[cyclobutane-1,5'-cyclopenta[d]pyridazin]-1'-yl)oxy)phenyl)-1,2,4-triazine-3,5(2H,4H)-dione;

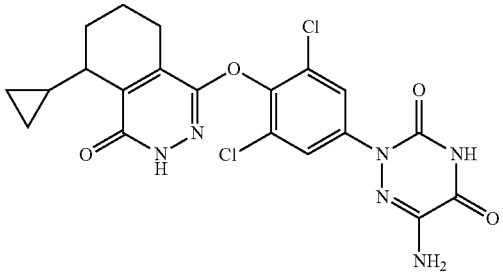 [SMILES: Nc1nn(-c2cc(Cl)c(Oc3n[nH]c(=O)c4c3CCCC4C3CC3)c(Cl)c2)c(=O)[nH]c1=O]

6-amino-2-(3,5-dichloro-4-((5-cyclopropyl-4-oxo-3,4,5,6,7,8-hexahydrophthalazin-1-yl)oxy)phenyl)-1,2,4-triazine-3,5(2H,4H)-dione;

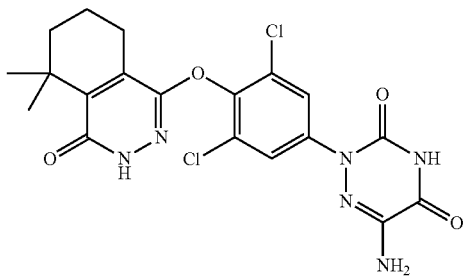 [SMILES: CC1(C)CCCc2c(Oc3c(Cl)cc(-n4nc(N)c(=O)[nH]c4=O)cc3Cl)n[nH]c(=O)c21]

6-amino-2-(3,5-dichloro-4-((5,5-dimethyl-4-oxo-3,4,5,6,7, 8-hexahydrophthalazin-1-yl)oxy)phenyl)-1,2,4-triazine-3,5(2H,4H)-dione;

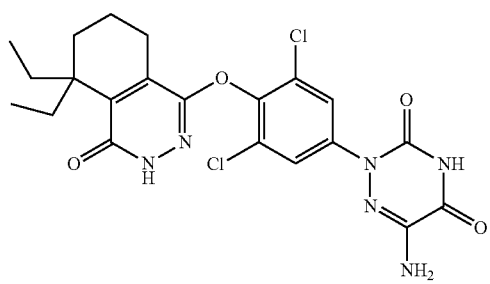 [SMILES: CCC1(CC)CCCc2c(Oc3c(Cl)cc(-n4nc(N)c(=O)[nH]c4=O)cc3Cl)n[nH]c(=O)c21]

6-amino-2-(3,5-dichloro-4-((5,5-diethyl-4-oxo-3,4,5,6,7,8-hexahydrophthalazin-1-yl)oxy)phenyl)-1,2,4-triazine-3,5(2H,4H)-dione;

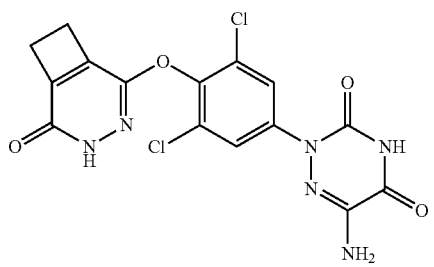 [SMILES: Nc1nn(-c2cc(Cl)c(Oc3n[nH]c(=O)c4c3CC4)c(Cl)c2)c(=O)[nH]c1=O]

6-amino-2-(3,5-dichloro-4-((5-oxo-3,4-diazabicyclo[4.2.0] octa-1(6),2-dien-2-yl)oxy)phenyl)-1,2,4-triazine-3,5(2H, 4H)-dione;

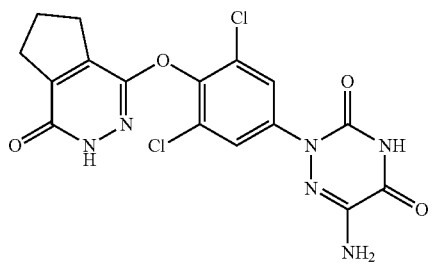 [SMILES: Nc1nn(-c2cc(Cl)c(Oc3n[nH]c(=O)c4c3CCC4)c(Cl)c2)c(=O)[nH]c1=O]

6-amino-2-(3,5-dichloro-4-((1-oxo-2,5,6,7-tetrahydro-1H-cyclopenta[d]pyridazin-4-yl)oxy)phenyl)-1,2,4-triazine-3,5(2H,4H)-dione;

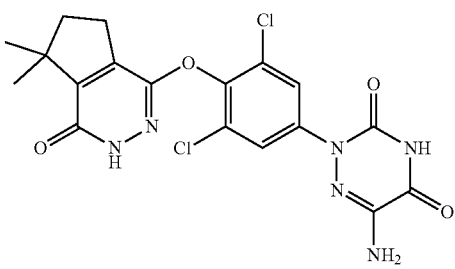 [SMILES: CC1(C)CCc2c(Oc3c(Cl)cc(-n4nc(N)c(=O)[nH]c4=O)cc3Cl)n[nH]c(=O)c21]

6-amino-2-(3,5-dichloro-4-((7,7-dimethyl-1-oxo-2,5,6,7-tetrahydro-1H-cyclopenta[d]pyridazin-4-yl)oxy)phenyl)-1,2,4-triazine-3,5(2H,4H)-dione;

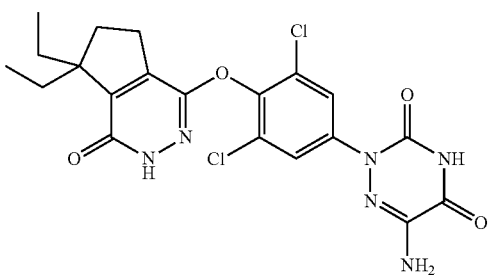 [SMILES: CCC1(CC)CCc2c(Oc3c(Cl)cc(-n4nc(N)c(=O)[nH]c4=O)cc3Cl)n[nH]c(=O)c21]

6-amino-2-(3,5-dichloro-4-((7,7-diethyl-1-oxo-2,5,6,7-tetrahydro-1H-cyclopenta[d]pyridazin-4-yl)oxy)phenyl)-1, 2,4-triazine-3,5(2H,4H)-dione;

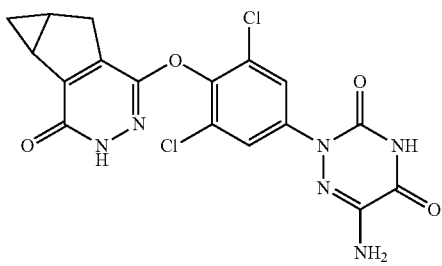 [SMILES: Nc1nn(-c2cc(Cl)c(Oc3n[nH]c(=O)c4c3CC3CC43)c(Cl)c2)c(=O)[nH]c1=O]

6-amino-2-(3,5-dichloro-4-((4-oxo-3,4,4b,5,5a,6-hexahydrocyclopropa[3,4]cyclopenta[1,2-d]pyridazin-1-yl)oxy) phenyl)-1,2,4-triazine-3,5(2H,4H)-dione;

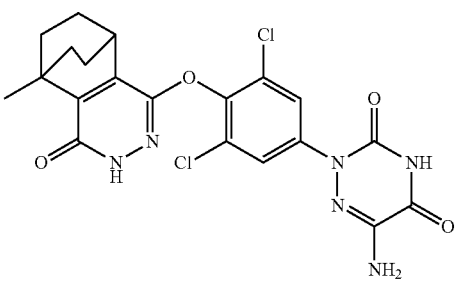 [SMILES: CC12CCC(CC1)c1c(Oc3c(Cl)cc(-n4nc(N)c(=O)[nH]c4=O)cc3Cl)n[nH]c(=O)c12]

6-amino-2-(3,5-dichloro-4-((5-methyl-4-oxo-3,4,5,6,7,8-hexahydro-5,8-ethanophthalazin-1-yl)oxy)phenyl)-1,2,4-triazine-3,5(2H,4H)-dione;

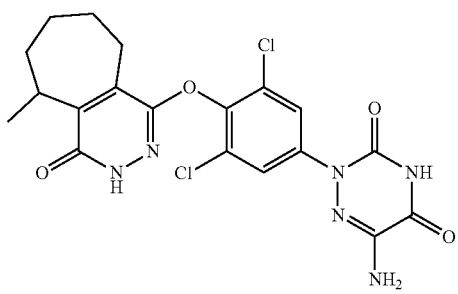 [SMILES: CC1CCCCc2c(Oc3c(Cl)cc(-n4nc(N)c(=O)[nH]c4=O)cc3Cl)n[nH]c(=O)c21]

6-amino-2-(3,5-dichloro-4-((9-methyl-1-oxo-2,5,6,7,8,9-hexahydro-1H-cyclohepta[d]pyridazin-4-yl)oxy)phenyl)-1,2,4-triazine-3,5(2H,4H)-dione;

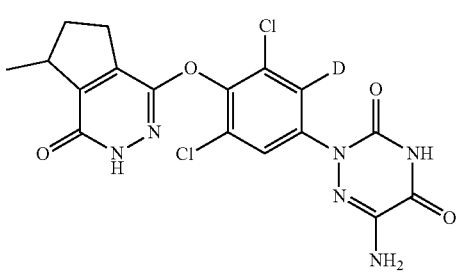

6-amino-2-(3,5-dichloro-4-((7-methyl-1-oxo-2,5,6,7-tetrahydro-1H-cyclopenta[d]pyridazin-4-yl)oxy)phenyl-2-d)-1,2,4-triazine-3,5(2H,4H)-dione;

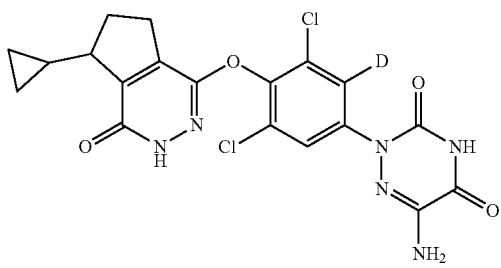 [SMILES: [2H]c1c(-n2nc(N)c(=O)[nH]c2=O)cc(Cl)c(Oc2n[nH]c(=O)c3c2CCC3C2CC2)c1Cl]

6-amino-2-(3,5-dichloro-4-((7-cyclopropyl-1-oxo-2,5,6,7-tetrahydro-1H-cyclopenta[d]pyridazin-4-yl)oxy)phenyl-2-d)-1,2,4-triazine-3,5(2H,4H)-dione;

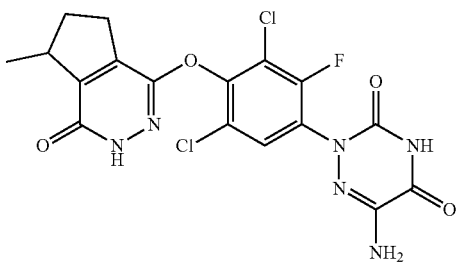 [SMILES: CC1CCc2c(Oc3c(Cl)cc(-n4nc(N)c(=O)[nH]c4=O)c(F)c3Cl)n[nH]c(=O)c21]

6-amino-2-(3,5-dichloro-2-fluoro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

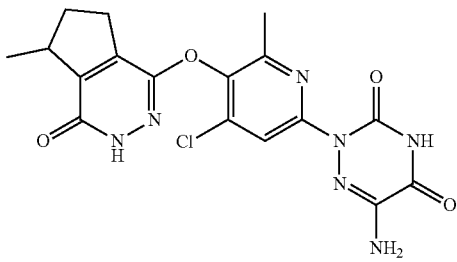 [SMILES: Cc1nc(-n2nc(N)c(=O)[nH]c2=O)cc(Cl)c1Oc1n[nH]c(=O)c2c1CCC2C]

6-amino-2-(4-chloro-6-methyl-5-((7-methyl-1-oxo-2,5,6,7-tetrahydro-1H-cyclopenta[d]pyridazin-4-yl)oxy)pyridin-2-yl)-1,2,4-triazine-3,5(2H,4H)-dione; and

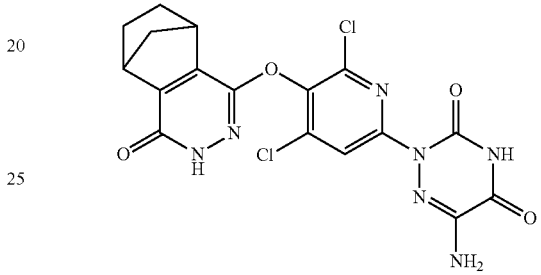

6-amino-2-(3,5-dichloro-4-((4-oxo-3,4,5,6,7,8-hexahydro-5,8-methanophthalazin-1-yl)oxy)phenyl)-1,2,4-triazine-3,5(2H,4H)-dione;

or a stereoisomer or a tautomer thereof, or a pharmaceutically acceptable salt thereof.

Synthesis of the Compounds

The presently disclosed compounds were synthesized using the general synthetic procedures set forth in Schemes below. The carrying out of each individual illustrated step is within the skill of an ordinary artisan, who also knows how to modify the synthetic procedures of the below schemes to synthesize the full scope of the compounds disclosed herein. The synthetic procedure for individual compounds is provided in the Examples section, below.

In Scheme 1, ketones may be condensed with a secondary amine (for example pyrrolidine) generating compounds of formula A1 containing a double bond suitable for the inverse electron demand Diels Alder reaction with dichloro-1,2,4,5-tetrazine to afford cyclized products of formula A2. For examples of the inverse electron demand Diels Alder reaction, see, e.g., J. Am. Chem. Soc. 2011, 133, 12285-12292, Org. Lett. 2014, 16, 5084-5087, and Tetrahedron Letters, Vol. 38, No. 22, pp. 3805-3808, 1997. Reaction of A2 and A3 with the aid of CuI and base (e.g. K$_2$CO$_3$) in a polar aprotic solvent (e.g. DMSO) affords compounds of formula A4. Hydrolysis of the chloropyridazine (for example with NaOAc, acetic acid at elevated temperature with a basic, aqueous workup) afford compounds A5, where the separation of potential regioisomers is facilitated.

Scheme 1.

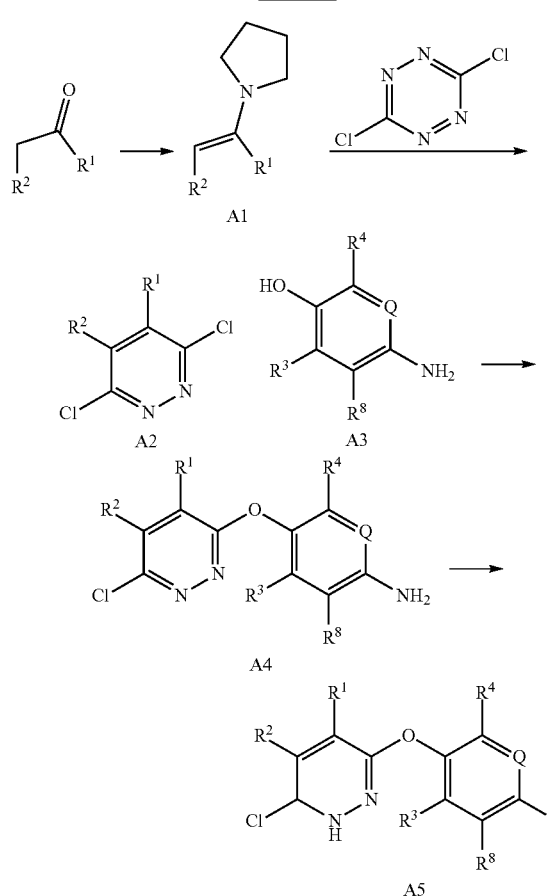

Scheme 2 describes the synthesis of compounds of Formula B3. Compounds of formula B1 (X=halogen), may be coupled with the phenolic compounds of formula B1a under a copper mediated coupling reaction in a polar aprotic solvent with base (e.g., $K_2CO_3$) at elevated temperature to afford intermediates of type B2. Alternatively, the coupling may take place with a Pd catalyst in an appropriate solvent with base. Subsequent deprotection of the protecting groups (Pg) leads to the formation of compounds of B3.

Scheme 2.

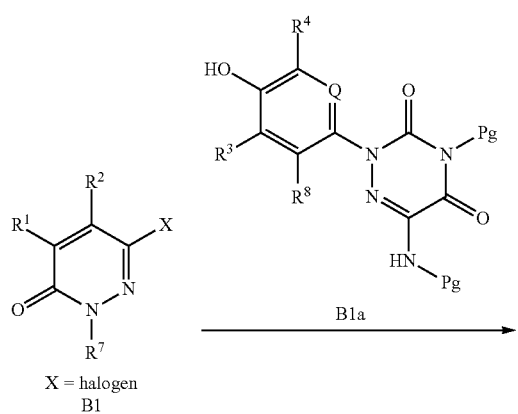

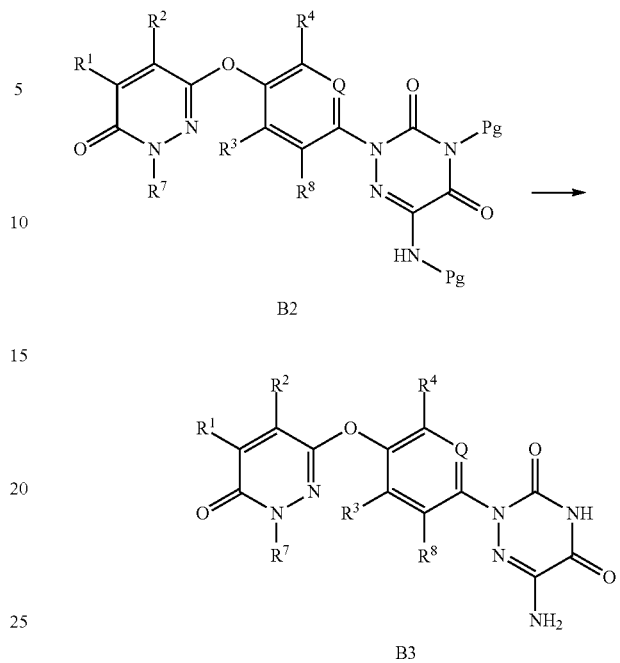

As described in Scheme 3, an aromatic amine compound of Formula C1 is converted to an aza-uracil compound of Formula C2, first by generating the corresponding diazonium salt, followed by reaction with an N-(2-cyanoacetyl)-carbamate, and then cyclization, results in the formation of a compound of Formula C2. Subsequent hydrolysis of the nitrile of Formula C2 to a carboxylic acid compound of Formula E3 using described conditions. The compounds of Formula C4 can be afforded from the acid compounds C3 proceeding through an acyl azide intermediate and subsequent Curtius rearrangement. Subsequent deprotection (of the protecting group Pg) of the compound of Formula C4, (for example if Pg is boc, using HCl or TFA), leads to compounds of formula C5.

Scheme 3.

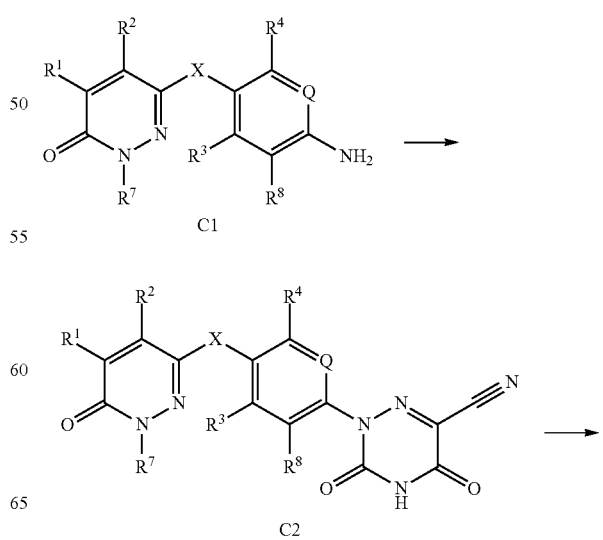

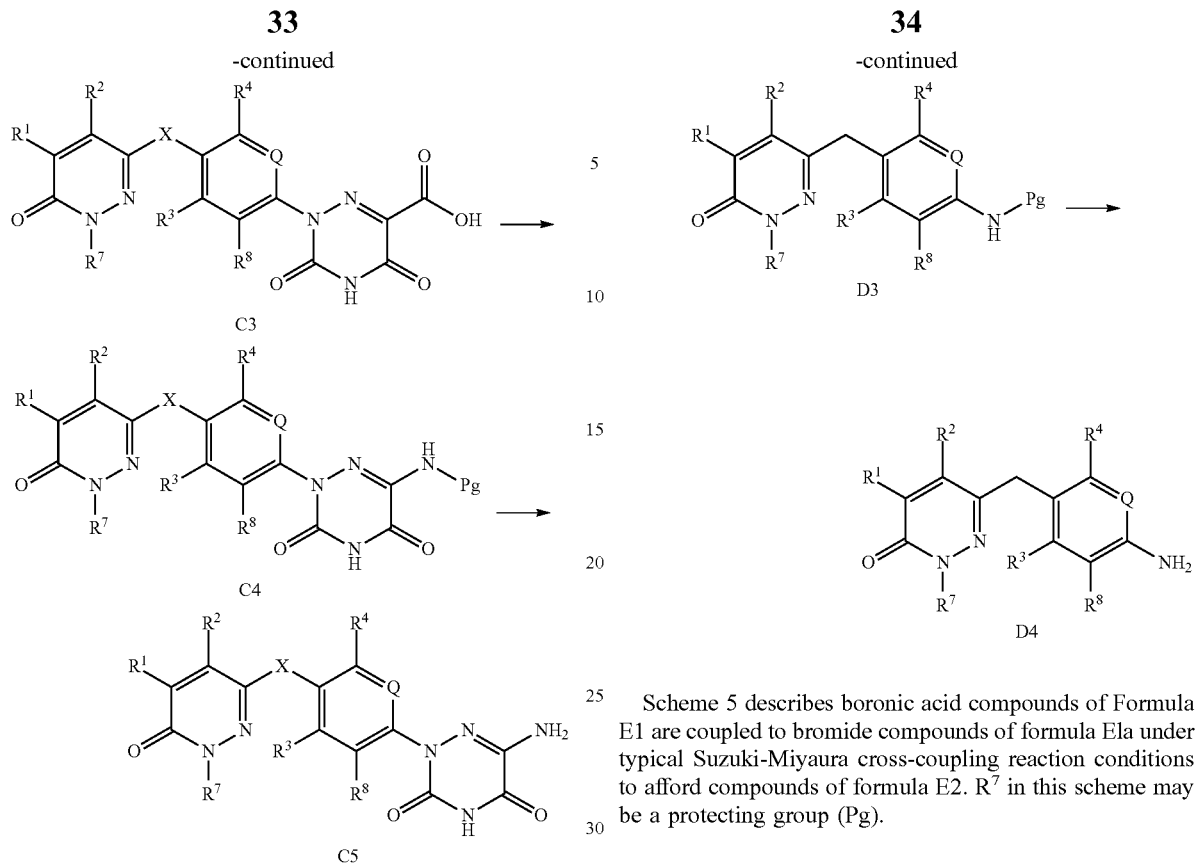

Scheme 4 describes the synthesis of a compound of Formula D4. A transmetalation reaction of a compound of Formula D1 (e.g., X is Br or I) is followed by an addition to the aldehyde of general formula D1a affording the alcohol compound of Formula D2, which is then reduced to a compound of Formula D3. Deprotection of Pg of the compound of Formula D3 results in the formation of a compound of Formula D4.

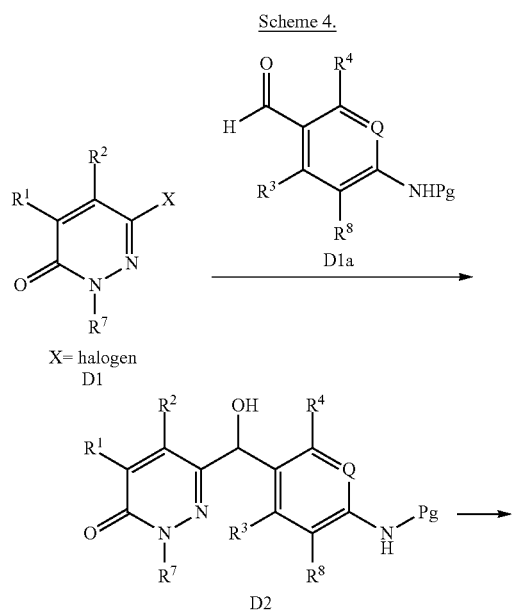

Scheme 5 describes boronic acid compounds of Formula E1 are coupled to bromide compounds of formula E1a under typical Suzuki-Miyaura cross-coupling reaction conditions to afford compounds of formula E2. $R^7$ in this scheme may be a protecting group (Pg).

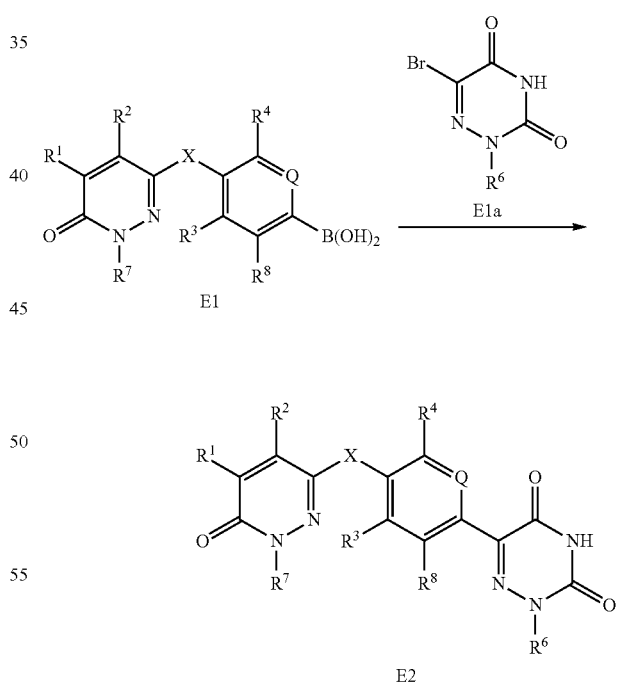

Scheme 6 depicts the synthesis of a compound of formula F2 from a compound of formula F1 in a Suzuki-Miyaura type coupling reaction with 4,4,5,5-tetramethyl-2-[(4,4,5,5-tetramethyl-1,3,2-dioxaborolan-2-yl)methyl]-1,3,2-dioxaborolane. An appropriate protecting group (Pg), or groups, may be required.

Scheme 6.

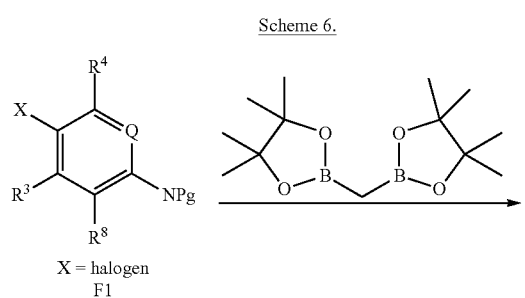

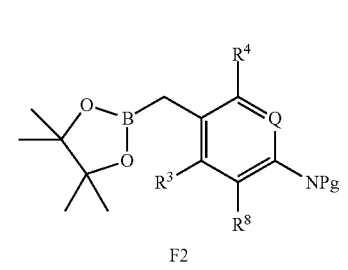

Scheme 7 describes the synthesis of a compound of Formula H6. The halogen (X) of nitrobenzene compounds H1 may be displaced by a cyanoacetate (e.g., tert-butyl 2-cyanoacetate) to afford compounds H2. Removal of the ester group and concomitant reduction of the nitro group could take place under conditions such as: $SnCl_2$, HCl, in ethanol at elevated temperature to afford H3. Under basic conditions H3 is reacted with compounds of formula H4 to yield compounds of formula H5. The CN group is subsequently removed under acidic conditions and elevated temperature to afford compounds of the formula H6.

Scheme 7.

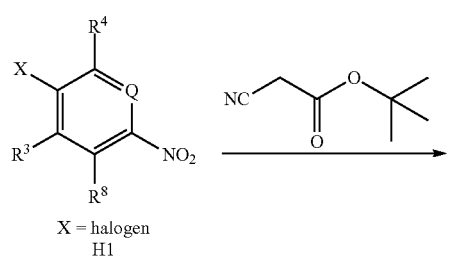

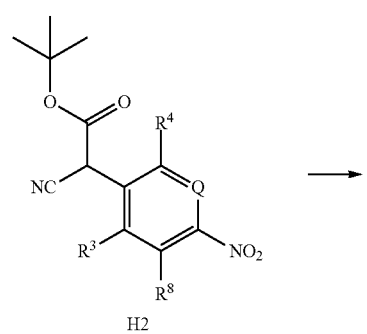

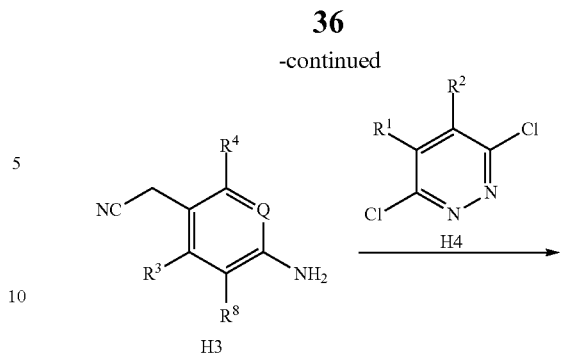

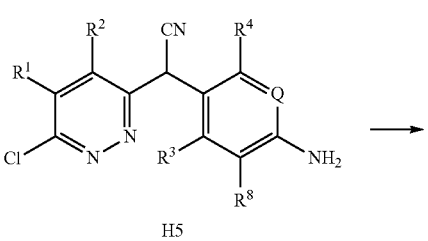

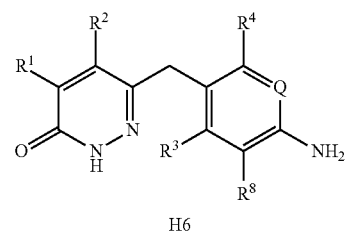

A compound of Formula K1 (Scheme 8) can be formed by reacting the aromatic amine of formula C1 with ethyl 2-chloro-2-oxoacetate in the presence of an organic base, in an appropriate organic solvent. Standard hydrolysis conditions are performed to afford compounds of formula K2. Compounds of the formula C1 may also be reacted with 5-oxo-4,5-dihydro-1,2,4-oxadiazole-3-carbonyl chloride in a non-polar organic solvent in the presence of a base to afford compounds of the formula K3. Alternatively, compounds of the formula C1 may also be reacted with 5-oxo-4,5-dihydro-1,2,4-oxadiazole-3-carboxylic acid in a polar aprotic solvent in the presence of a base and coupling agent to afford compounds of the formula K3. Compounds of the formula K4 may be produced by reaction of compounds of formula C1 with 5-oxo-4,5-dihydro-1,2,4-oxadiazole-3-carbaldehyde under standard reductive amination conditions. Alternatively, compounds of the formula K4 may be produced by reaction of compounds of formula C1 with 3-(bromomethyl)-1,2,4-oxadiazol-5(4H)-one (or, for example, 3-(chloromethyl)-1,2,4-oxadiazol-5(4H)-one) under basic conditions with optional heating.

Scheme 8.

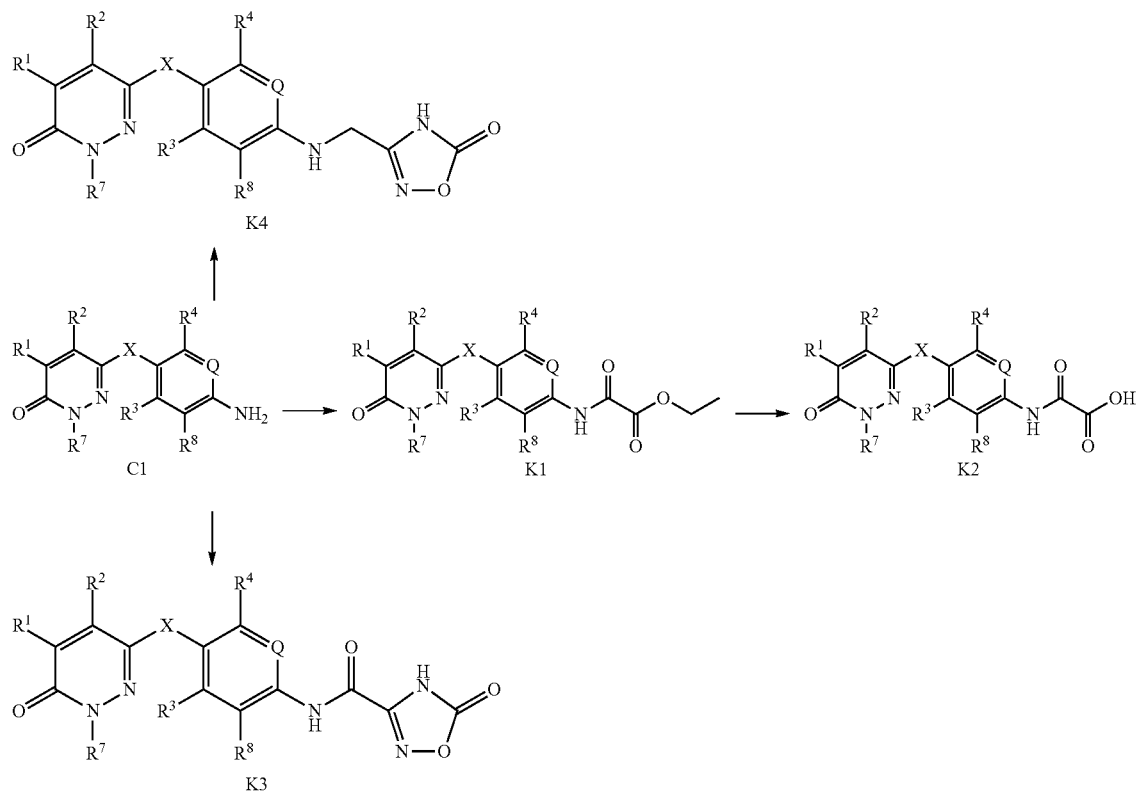

Scheme 9 depicts the synthesis of compounds of formula M3. The aryl halide compounds M1 are reacted with methyl propiolate under typical Sonogoshira conditions to afford compounds of formula M2. Cyclization towards heterocycles of the formula M3 occurs under conditions described in the literature (e.g., J. Med. Chem. 2002, 45, 9, 1785-1798; J. Med. Chem. 2013, 56, 5, 1894-1907). Compounds of formula M3 can alternatively be generated via other described methods (e.g., J. Org. Chem. 2000, 65, 4, 1003-1007; J. Med. Chem. 1989, 32, 9, 2116-2128).

Scheme 9.

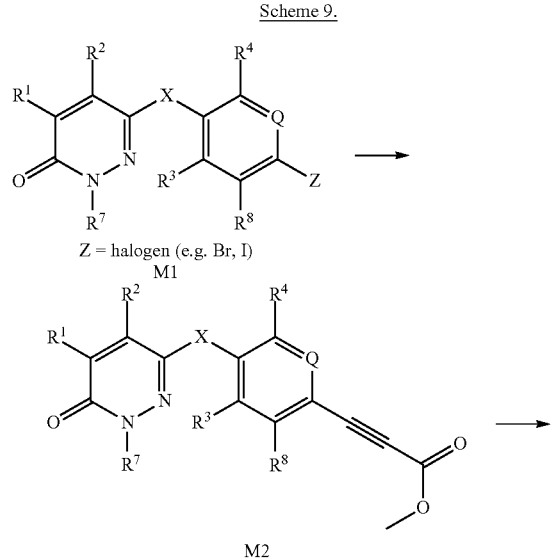

-continued

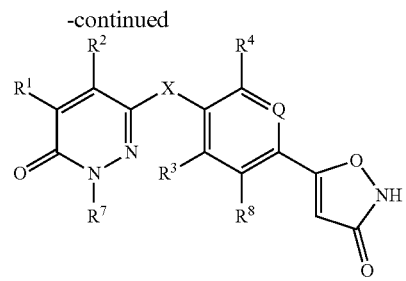

Scheme 10 describes the synthesis of compounds of formula M12. Aryl cyanide compounds M10 can be transformed to compounds of formula M11 via the addition of hydroxylamine. Further conversion to compounds of formula M12 proceeds via the addition of carbonyl diimidazole with base in an appropriate solvent, often at elevated temperature (see, e.g., Molecular Pharmaceutics, 16(4), 1489-1497; 2019). Compounds of the formula M10 may be synthesized from the aryl halides M1 via several described methods using either a copper catalyst (known as the Rosenmund-von Braun reaction) or alternatively using a Pd catalyst (see, e.g., J. Am. Chem. Soc., 2011, 133, 10999-11005). The aryl cyanides of formula M10 may also be generated from the amine using the Sandmeyer reaction.

Scheme 10.

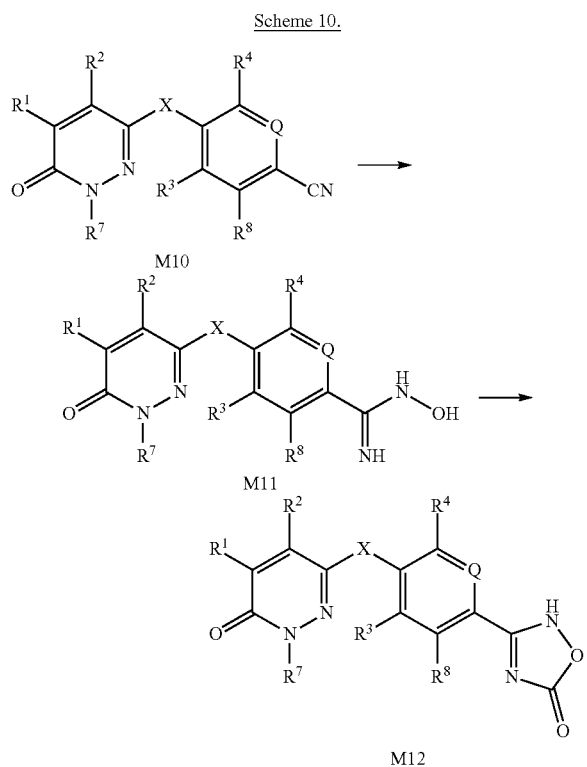

Pharmaceutical Compositions

In another aspect, disclosed herein are pharmaceutical compositions comprising, consisting essentially of, or consisting of a compound as described herein, and at least one pharmaceutically acceptable excipient.

In another aspect, disclosed herein are pharmaceutical compositions comprising, consisting essentially of, or consisting of a compound of Formula I, as described herein, and at least one pharmaceutically acceptable excipient.

The pharmaceutical composition disclosed herein may comprise a pharmaceutically acceptable carrier, such as diluents, disintegrants, sweetening agents, glidants, or flavoring agents and may be formulated into an oral dosage form such as tablets, capsules, powders, granules, suspensions, emulsions, or syrups; or a parenteral dosage form such as liquids for external use, suspensions for external use, emulsions for external use, gels (ointments or the like), inhaling agents, spraying agents, injections, etc. Said dosage forms may be formulated in various forms, e.g., a dosage form for single administration or for multiple administrations.

The pharmaceutical composition disclosed herein may include excipients such as lactose, corn starch, or the like, glidants such as magnesium stearate, etc., emulsifying agents, suspending agents, stabilizers, and isotonic agents, etc. If desired, a sweetening agent and/or a flavoring agent may be added. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Inorganic salt or buffers include, but are not limited to, citric acid, sodium chloride, potassium chloride, sodium sulfate, potassium nitrate, sodium phosphate monobasic, sodium phosphate dibasic, and combinations thereof.

Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition disclosed herein may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Generally, however, the excipient will be present in the composition in an amount of about 1% to about 99% by weight, preferably from about 5% to about 98% by weight, more preferably from about 15 to about 95% by weight of the excipient. In general, the amount of excipient present in a composition of the disclosure is selected from the following: at least about 2%, 5%0, 10%, 15%, 20%, 25%, 30%, 35%, 40%, 45%, 50%, 55%, 60%, 65%, 70%, 75%, 80%, 85%, 90%, or even 95% by weight.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, transdermal, rectal, transmucosal, or intestinal administration; parenteral delivery, including intramuscular, subcutaneous, intravenous, intramedullary injections, as well as inhalation, intrathecal, direct intraventricular, intraperitoneal, intranasal, or intraocular injections.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. These pharmaceutical compositions, then, may be formulated in a conventional manner using one or more known physiologically acceptable carriers comprising excipients and/or auxiliaries, which facilitate processing of the active compounds into preparations that can be used pharmaceutically. Any of the well-known techniques, carriers, and excipients may be used as suitable and as understood in the art; e.g., in Remington's Pharmaceutical Sciences, above.

Pharmaceutical compositions suitable for use in the presently disclosed formulations include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. In some embodiments, a therapeutically effective amount means an amount of compound effective to alleviate or ameliorate symptoms of disease or prolong the survival of the subject being treated.

Although the exact dosage can be determined on a drug-by-drug basis, in most cases, some generalizations regarding the dosage can be made. The daily dosage regimen for an adult human patient may be, for example, an oral dose of between 0.001 mg and 1000 mg of each ingredient, preferably between 0.01 mg and 500 mg, for example 1 to 200 mg or each active ingredient of the pharmaceutical compositions disclosed herein or a pharmaceutically acceptable salt thereof calculated as the free base or free acid, the composition being administered 1 to 4 times per day or per week. Alternatively, the compositions disclosed herein may be administered by continuous such as sustained, delayed, or extended release, preferably at a dose of each ingredient up to 500 mg per day. Thus, the total daily dosage by oral administration of each ingredient will typically be in the range 0.1 mg to 2000 mg.

Methods of Treatment

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound as described herein.

In another aspect, disclosed herein are methods of treating a thyroid hormone receptor related disorder in a patient, the method comprising, consisting essentially of, or consisting of the steps of identifying a patient in need of treatment for the thyroid hormone receptor related disorder, and administering to the patient, or contacting the patient with, a compound of Formula I, as described herein.

In some embodiments, a health care professional, such as a physician, physician's assistant, nurse practitioner, or the like, identifies an individual as being in need of treatment for the thyroid hormone receptor related disorder, and/or a candidate for treatment with a compound disclosed herein. The identification may be based on medical test results, non-responsiveness to other, first-line therapies, the specific nature of the particular liver disorder, or the like.

In some embodiments, the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating a disorder or disease in a subject in need thereof, the method comprising, consisting essentially of, or consisting of administering to the subject a therapeutically effective amount of a compound or composition disclosed herein, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

In another aspect, disclosed herein are methods of treating NASH in a subject in need thereof, the method comprising, consisting essentially of, or consisting of administering to the subject a therapeutically effective amount of a compound or composition disclosed herein.

In another aspect, disclosed herein are methods of treating obesity in a subject in need thereof, the method comprising, consisting essentially of, or consisting of administering to the subject a therapeutically effective amount of a compound or composition disclosed herein.

In another aspect, disclosed herein are methods of treating hyperlipidemia in a subject in need thereof, the method comprising, consisting essentially of, or consisting of administering to the subject a therapeutically effective amount of a compound or composition disclosed herein.

In another aspect, disclosed herein are methods of treating hypercholesterolemia in a subject in need thereof, the method comprising, consisting essentially of, or consisting of administering to the subject a therapeutically effective amount of a compound or composition disclosed herein.

In another aspect, disclosed herein are methods of treating diabetes in a subject in need thereof, the method comprising, consisting essentially of, or consisting of administering to the subject a therapeutically effective amount of a compound or composition disclosed herein.

In another aspect, disclosed herein are methods of treating liver steatosis in a subject in need thereof, the method comprising, consisting essentially of, or consisting of administering to the subject a therapeutically effective amount of a compound or composition disclosed herein.

In some embodiments, the compound of Formula I, as described herein, or the stereoisomer or the tautomer thereof, or the pharmaceutically acceptable salt thereof, or a therapeutically effective amount of the pharmaceutical composition; is administered in combination with a KHK inhibitor, an FXR agonist, a SSAO inhibitor, a FASN inhibitor, or a SCD1 modulator. In some embodiments, the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

In another aspect, disclosed herein are methods of selectively modulating the activity of a thyroid hormone receptor beta (THR-β) comprising, consisting essentially of, or consisting of contacting a compound as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a compound of Formula I, as described herein, with a thyroid hormone receptor. In some embodiments, the contacting is in vitro or ex vivo, whereas in other embodiments, the contacting is in vivo.

In another aspect, disclosed herein are methods of selectively modulating the activity of a thyroid hormone receptor beta (THR-β) comprising, consisting essentially of, or consisting of contacting a composition described herein, with a thyroid hormone receptor. In some embodiments, the contacting is in vitro or ex vivo, whereas in other embodiments, the contacting is in vivo.

EXAMPLES

Example 1. Preparation of Compounds 1a and 1b

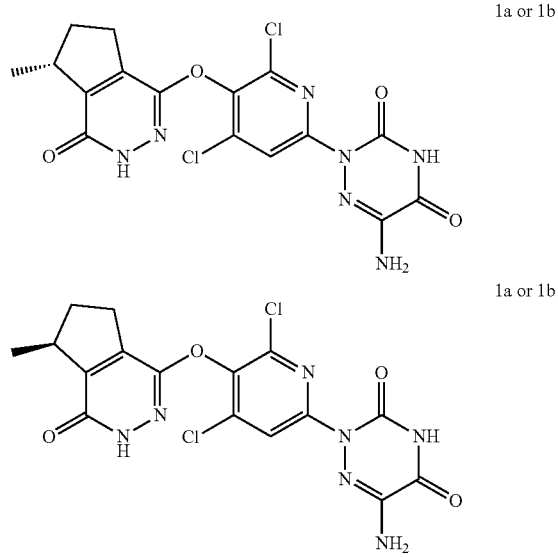

A solution of 2-methylcyclopentan-1-one (6.00 g, 61.1 mmol) pyrrolidine (6.52 g, 91.7 mmol) and TsOH (1.16 g, 6.11 mmol) in toluene (70 mL) was refluxed for overnight under N2. The resulting solution was concentrated under reduced pressure to provide 6 g of 1-(5-methylcyclopent-1-en-1-yl)pyrrolidine as a white solid. LC-MS (ESI, m/z): 152 [M+H]$^+$. The crude product was used in the next step without further purification.

A solution of dichloro-1,2,4,5-tetrazine (3.00 g, 19.9 mmol) and 1-(5-methylcyclopent-1-en-1-yl)pyrrolidine (6.01 g, 39.7 mmol) in toluene (100 mL) was stirred for overnight at 80° C. under N2. The resulting mixture was concentrated under reduced pressure. The residue was chromatographed on a silica gel column with petroleum ether/ ethyl acetate (19/1) to provide 1.5 g (yield 37%) of 1,4-dichloro-5-methyl-5H,6H,7H-cyclopenta[d]pyridazine as a pink solid. LC-MS (ESI, m/z): 203 [M+H]$^+$.

To a solution of 1,4-dichloro-5-methyl-5H,6H,7H-cyclopenta[d]pyridazine (1.00 g, 4.92 mmol) in dimethyl sulfoxide (20 mL) were added 4-amino-2,6-dichlorophenol (964 mg, 5.42 mmol), K$_2$CO$_3$ (1.36 g, 9.85 mmol), CuI (468 mg, 2.46 mmol) in portions. The resulting mixture was stirred overnight at 90° C. for 16 h under nitrogen atmosphere and quenched with water (60 mL). The resulting mixture was extracted with ethyl acetate (3×50 mL). The combined organic layers were washed with brine (100 mL), dried over anhydrous Na$_2$SO$_4$, the solids were removed by filtration and the filtrate was concentrated under reduced pressure to provide 1 g of 3,5-dichloro-4-([4-chloro-5-methyl-5H,6H,7H-cyclopenta[d]pyridazin-1-yl]oxy)aniline as a brown solid. LC-MS (ESI, m/z): 344 [M+H]$^+$. The crude product was used in the next step without further purification.

To a solution of 3,5-dichloro-4-({4-chloro-5-methyl-5H,6H,7H-cyclopenta[d]pyridazin-1-yl}oxy)aniline (850 mg, 2.45 mmol) in acetic acid (10 mL) was added sodium acetate (1.01 g, 12.3 mmol). The mixture was stirred overnight at 100° C. The resulting mixture was concentrated and diluted with water (50 mL). The mixture was adjusted to pH 9 with NaOH (aq., 1 M). The resulting solution was extracted with ethyl acetate (3×50 mL) and the combined organic layers were concentrated under reduced pressure then dissolved in CH$_3$OH (5 mL) and NaOH (834 mg, 20.9 mmol) in water (5 mL). The resulting mixture was stirred overnight at 120° C. The resulting mixture was concentrated and extracted with ethyl acetate (3×50 mL). The combined organic layers were washed with brine (100 mL), dried over anhydrous Na$_2$SO$_4$, the solids were removed by filtration and the filtrate was concentrated under reduced pressure. The residue was chromatographed on a silica gel column with petroleum ether/ ethyl acetate to provide 250 mg (yield 31%) of 4-(4-amino-2,6-dichlorophenoxy)-7-methyl-2H,5H,6H,7H-cyclopenta[d]pyridazin-1-one as a brown solid. $^1$H NMR (300 MHz, DMSO-d$_6$) δ 12.01 (s, 1H), 6.62 (s, 2H), 5.59 (s, 2H), 3.19-3.29 (m, 1H), 2.78-2.99 (m, 2H), 2.29-2.39 (m, 1H), 1.61-1.72 (m, 1H), 1.23 (d, J=6.0 Hz, 3H). LC-MS (ESI, m/z): 326 [M+H]$^+$.

To a solution of 4-(4-amino-2,6-dichlorophenoxy)-7-methyl-2H,5H,6H,7H-cyclopenta[d]pyridazin-1-one (200 mg, 0.613 mmol), water (12 mL), HCl (conc., 5 mL) and acetic acid (15 mL) was added sodium nitrite (84.6 mg, 1.22 mmol) in water (5 mL) dropwise at 0° C. After the addition, the reaction was stirred at 0° C. for 45 min. Then the reaction mixture was added to a solution of ethyl N-(2-cyanoacetyl)carbamate (143 mg, 0.919 mmol) in water (12 mL) and pyridine (5 mL) at 0° C. quickly. The resulting mixture was stirred at 0° C. for 1 h and filtered. The filter cake was washed with water (30 mL) and petroleum ether (30 mL), dried under the IR lamp to provide 190 mg of ethyl (2-cyano-2-(2-(3,5-dichloro-4-((7-methyl-1-oxo-2,5,6,7-tetrahydro-1H-cyclopenta[d]pyridazin-4-yl)oxy)phenyl)hydrazineylidene)acetyl)carbamate as an orange solid. LC-MS (ESI, m/z): 493 [M+H]$^+$. The crude product was used in the next step without further purification.

To a solution of ethyl (2-cyano-2-(2-(3,5-dichloro-4-((7-methyl-1-oxo-2,5,6,7-tetrahydro-1H-cyclopenta[d] pyridazin-4-yl)oxy)phenyl)hydrazineylidene)acetyl)carbamate (190 mg, 0.385 mmol) in DMA (8 mL) was added K$_2$CO$_3$ (189 mg, 1.93 mmol). The reaction was stirred at 120° C. for 2 h and cooled to room temperature. The resulting mixture was quenched with water (30 mL) and extracted with ethyl acetate (3×30 mL). The combined organic layers were washed with brine (50 mL), dried over anhydrous Na$_2$SO$_4$. After filtration, the filtrate was concentrated under reduced pressure to provide 180 mg of 2-[3,5-dichloro-4-({5-methyl-4-oxo-3H,5H,6H,7H-cyclopenta[d] pyridazin-1-yl}oxy)phenyl]-3,5-dioxo-4H-1,2,4-triazine-6-carbonitrile as a red solid. LC-MS (ESI, m/z): 447 [M+H]$^+$. The crude product was used in the next step without further purification.

A solution of 2-[3,5-dichloro-4-({5-methyl-4-oxo-3H,5H, 6H,7H-cyclopenta[d]pyridazin-1-yl}oxy)phenyl]-3,5-dioxo-4H-1,2,4-triazine-6-carbonitrile (180 mg, 0.402 mmol) in HCl (2 mL) was added acetic acid (4 mL). The resulting mixture was stirred 4 h at 100° C. and concentrated reduced pressure. The residue was diluted with NaHCO$_3$ (aq., 20 mL), the resulting mixture was extracted with ethyl acetate (2×15 mL) and the organic layers were discarded. The pH value of the aqueous layers was adjusted to 6 with HCl (conc.). The resulting solution was extracted with ethyl acetate (3×15 mL). The precipitate was generated, isolated by filtration, and dried under reduced pressure to provide 100 mg of 2-[3,5-dichloro-4-({5-methyl-4-oxo-3H,5H,6H,7H-cyclopenta[d]pyridazin-1-yl}oxy)phenyl]-3,5-dioxo-4H-1,2,4-triazine-6-carboxylic acid as a brown solid. LC-MS (ESI, m/z): 466 [M+H]+. The crude product was used in the next step without further purification.

To a solution of 2-[3,5-dichloro-4-({5-methyl-4-oxo-3H,5H,6H,7H-cyclopenta[d]pyridazin-1-yl}oxy)phenyl]-3,5-dioxo-4H-1,2,4-triazine-6-carboxylic acid (100 mg, 0.214 mmol) in t-butanol (5 mL) was added triethylamine (108 mg, 1.07 mmol) and diphenylphosphoryl azide (DPPA, 177 mg, 0.642 mmol). The reaction was stirred at 85° C. overnight then concentrated under reduced pressure. The residue was dissolved in ethyl acetate (40 mL) and washed with NaHCO3 (aq., 40 mL) and brine (40 mL), dried over anhydrous Na2SO4. The solids were removed by filtration, the filtrate was concentrated under reduced pressure to provide 80 mg of t-butyl N-{2-[3,5-dichloro-4-({5-methyl-4-oxo-3H,5H,6H,7H-cyclopenta[d]pyridazin-1-yl}oxy)phenyl]-3,5-dioxo-4H-1,2,4-triazin-6-yl}carbamate as a brown solid. LC-MS (ESI, m/z): 537 [M+H]+. The crude product was used in the next step without further purification.

To a solution of t-butyl N-{2-[3,5-dichloro-4-({5-methyl-4-oxo-3H,5H,6H,7H-cyclopenta[d]pyridazin-1-yl}oxy)phenyl]-3,5-dioxo-4H-1,2,4-triazin-6-yl}carbamate (80.0 mg, 14.9 mmol) in CH2Cl2 (2 mL) was added trifluoroacetic acid (2 mL). The reaction was stirred at room temperature for 4 h and concentrated under reduced pressure. The crude product (80 mg) was purified by reverse phase prep LC. Column: XBridge Prep Phenyl OBD Column, 5 mm, 19×250 mm; Mobile Phase A: Water (10 mmol/L NH4HCO3+0.1% NH3·H2O), Mobile Phase B: CH3CN; Flow rate: 25 mL/min; Gradient: 20% B to 42% B in 7 min; 210 nm; to provide 24 mg (yield 36%) of 6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione. LC-MS (ESI, m/z): 437 [M+H]+.

The enantiomers were purified by prep-chiral chromatography (Column: CHIRALPAK IA, 2×25 cm, 5 mm; Mobile Phase A: HEX: DCM=3:1 (0.1% DEA). HPLC, Mobile Phase B: EtOH. Flow rate: 20 mL/min; Gradient: 20% B to 20% B in 30 min; collected at 220/254 nm; Rt 1: 11.841 min; Rt 2: 14.619 min; Injection Volume: 0.5 mL). 1H NMR (400 MHz, DMSO-d6) δ 7.88 (s, 2H), 6.33 (s, 2H), 3.10-3.22 (m, 1H), 2.88-3.09 (m, 2H), 2.31-2.43 (m, 1H), 1.64-1.84 (m, 1H), 1.26 (d, J=8.0 Hz, 3H). The first eluting enantiomer afforded compound 1a, (6 mg, 30% yield) of a white solid. LC-MS Method A, Rt: 0.629 min (ESI, m/z): 437 [M+H]+. The second eluting enantiomer afforded compound 1b (4.9 mg, 29% yield) of a white solid. LC-MS Method A, Rt: 0.621 min (ESI, m/z): 437 [M+H]+. The absolute stereochemistry of the enantiomers was not established.

Compounds 2a/2b and 3a/3b can be synthesized in a similar manner as that described for compounds 1a/1b.

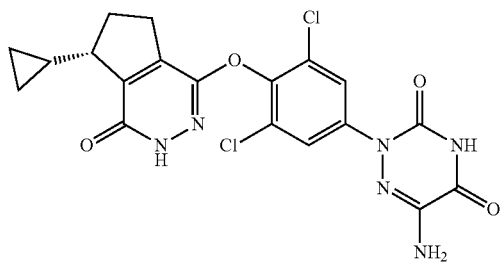

2a or 2b

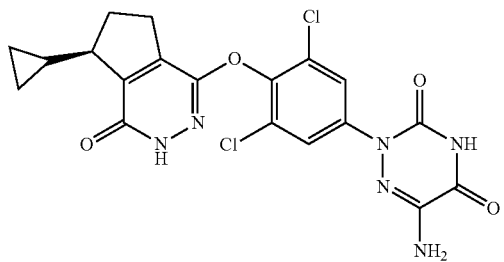

2a or 2b

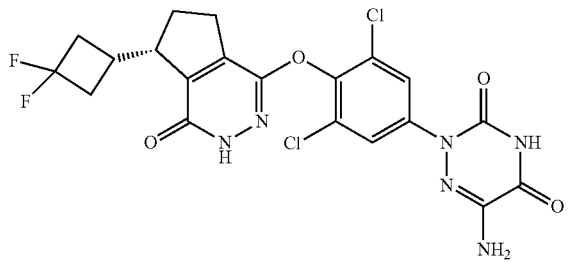

3a or 3b

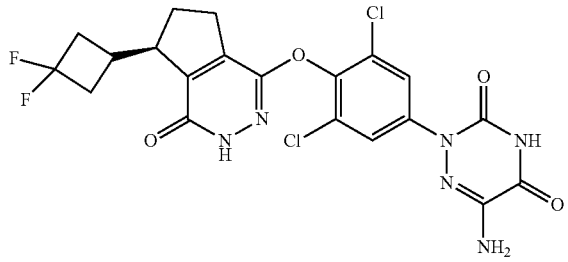

3a or 3b

LC-MS Methods

| LC Method name | Instrument | Column | Mobile phase | Gradient | Flow | Col T (° C.) | Run time |
|---|---|---|---|---|---|---|---|
| A | Shimadzu LCMS-2020 | Kinetex EVO C18 (2.6 µm, 3.0 × 30 mm) | A: Water/6.5 mM NH4HCO3 + NH4 OH (pH = 10) B: CH3CN | From 90% A to 5% A in 1.19 min, held for 0.6 min, to 90% A in 0.02 min, held for 0.18 min | 1.2 mL/min | 40 | 2 min |

Biological Assays

THR Biochemical Assay (Assay 1)

The TR-FRET thyroid receptor beta coactivator assay was used with slight, optimized modifications of the manufacturer's protocol (Invitrogen). The assay uses a terbium-labeled anti-GST antibody, a glutathione-S-transferase (GST) tagged human thyroid receptor, beta or alpha, ligand-binding domain (LBD), and a fluorescein labeled SRC2-2 coactivator peptide. The antibody interacts with the LBD, where the agonist also binds, resulting in increased affinity for the SRC2-2 coactivator peptide causing energy transfer of the acceptor fluorophore and a FRET emission shift from 495 to 520 nm. The energy transfer was detected as an increase in the fluorescence emission of the fluorescein acceptor, and a decrease in the fluorescence emission of the terbium donor. The assay was performed in a 384-well black plate in a final volume of 20 µL. Serial dilution of various test agonists was performed in DMSO (1% final DMSO concentration) and added to the test plate. Thyroid receptor beta LBD was added to the plate at a final concentration of 1 nM, followed by the mixture of the fluorescein labeled SRC2-2 coactivator peptide, and the terbium-labeled anti-GST antibody at final concentrations of 200 nM and 2 nM respectively. The assay was incubated for 1 hr at rt protected from light. The TR-FRET was then measured on a Victor multilabel reader (Perkin Elmer) using an excitation wavelength of 340 nm with emission filters of 495 nm and 520 nm. The assay was quantified by expressing a ratio (520:495) of the intensities, and the resulting activation curves; $EC_{50}$ values were generated using a sigmoidal dose response (variable slope) equation in GraphPad™ Prism 8.0.

Compounds of Formula (I) are active as THR-beta agonists as shown in Table 1, where: for Assay 1: 'A' indicates an $EC_{50}$<50 nM, 'B' indicates an $EC_{50}$ of >50 nM and <250 nM, 'C' indicates an $EC_{50}$>250 nM and <1000 nM, 'D' indicates an $EC_{50}$>1000 nM and <25000 nM, and 'E' indicates an $EC_{50}$>25000 nM.

TABLE 1

| Compound number | Assay 1 |
| --- | --- |
| 1a | A |
| 1b | B |

Diet-Induced Obese (DIO) Mouse Model of NASH

C57BL/6J mice are fed a high-fat diet for 10 weeks to induce obesity and injected intraperitoneally twice weekly with carbon tetrachloride ($CCl_4$) for an additional 4 weeks to induce fibrosis. Mice fed a normal chow diet are used as healthy controls. Concomitant with $CCl_4$ dosing, mice are treated with vehicle or with a compound disclosed herein, administered by oral gavage once daily for 28 days. Drug exposure is measured in a separate experiment in lean male C57BL/6J mice. Livers of mice in the NASH study are harvested and evaluated for liver steatosis and fibrosis by histology and whole transcriptome analysis in the liver using RNA sequencing. Target engagement is confirmed by monitoring expression of TRβ-regulated genes.

Human Clinical Study: NASH

In a randomized, double-blind, placebo-controlled study, adult patients (with biopsy confirmed NASH (fibrosis stages 1-3) and hepatic fat fraction of at least 10% at baseline when assessed by MRI-proton density fat fraction (MRI-PDFF) are administered a compound disclosed herein or placebo. Serial hepatic fat measurements are obtained at weeks 12 and 36, and a second liver biopsy is obtained at week 36. The primary endpoint is relative change in MRI-PDFF assessed hepatic fat compared with placebo at week 12 in patients who have both a baseline and week 12 MRI-PDFF.

REFERENCES

1. Younossi, Z M, Koenig, A B, Abdelatif, D, Fazel, Y, Henry, L, Wymer, M. Global epidemiology of nonalcoholic fatty liver disease-Meta-analytic assessment of prevalence, incidence, and outcomes. Hepatology, 2016, 64(1):73e84.
2. Gastroenterology. 2012 June; 142(7): 1592-609. doi: 10.1053/j.gastro.2012.04.001. Epub 2012 May 15.
3. Serfaty, L., Lemoine, M. Definition and natural history of metabolic steatosis: clinical aspects of NAFLD, NASH and cirrhosis. Diabetes and Metabolism, 2008, 34 (6 Pt 2):634e637.
4. Hepatology. 2012 October; 56(4): 1580-1584. doi: 10.1002/hep.26031
5. Dulai, P S, Singh, S, Patel, J, Soni, M, Prokop, L J, Younossi, Z, et al. Increased risk of mortality by fibrosis stage in nonalcoholic fatty liver disease: systematic review and meta-analysis. Hepatology, 2017, 65(5): 1557e1565.
6. Younossi, Z M, Loomba, R, Rinella, M E, Bugianesi, E, Marchesini, G, Neuschwander-Tetri, B A, et al. Current and future therapeutic regimens for non-alcoholic fatty liver disease (NAFLD) and non-alcoholic steatohepatitis (NASH). Hepatology, 2018, 68(1):349e360.
7. Harvey C B, Williams G R. Mechanism of thyroid hormone action. Thyroid, 2002 June; 12(6):441-6.
8. Bookout A L, Jeong Y, Downes M, Yu R T, Evans R M, Mangelsdorf D J. Anatomical profiling of nuclear receptor expression reveals a hierarchical transcriptional network. Cell, 2006, 126:789-799
9. Flamant F, Baxter J D, Forrest D, Refetoff S, Samuels H H, Scanlan T S, Vennstrom B, Samarut J. International union of pharmacology. LIX. The pharmacology and classification of the nuclear receptor superfamily: thyroid hormone receptors. Pharmacol. Rev., 2006, 58:705-711
10. Haning H, Woltering M, Mueller U, Schmidt G, Schmeck C, Voehringer V, Kretschmer A, Pernerstorfer J. Bioorg. Med Chem Lett., 2005 Apr. 1, 15(7): 1835-40. Novel heterocyclic thyromimetics.
11. Hirano T, Kagechika H. Thyromimetics: a review of recent reports and patents (2004-2009). Expert Opin Ther Pat., 2010 February; 20(2):213-28. doi: 10.1517/13543770903567069.
12. Kowalik M A, Columbano A, Perra A. Thyroid Hormones, Thyromimetics and Their Metabolites in the Treatment of Liver Disease. Front Endocrinol (Lausanne), 2018 Jul. 10; 9:382. doi: 10.3389/fendo.2018.00382. eCollection 2018.
13. Erion M D, Cable E E, Ito B R, Jiang H, Fujitaki J M, Finn P D, Zhang B H, Hou J, Boyer S H, van Poelje P D, Linemeyer D L. Targeting thyroid hormone receptor-beta agonists to the liver reduces cholesterol and triglycerides and improves the therapeutic index. Proc Natl Acad Sci USA., 2007 Sep. 25; 104(39):15490-5. Epub 2007 Sep. 18.
14. Hartley M D, Kirkemo L L, Banerji T, Scanlan T S. A Thyroid Hormone-Based Strategy for Correcting the Biochemical Abnormality in X-Linked Adrenoleukodystrophy. Endocrinology 2017, 158(5), p 1328-1338. doi: 10.1210/en.2016-1842.
15. Milanesi A, Brent G A. Beam Me In: Thyroid Hormone Analog Targets Alternative Transporter in Mouse Model of X-Linked Adrenoleukodystrophy. Endocrinology 2017, 158, p 1116-1119. doi: 10.1210/en.2017-00206.

EMBODIMENTS

Embodiment P1. A compound of Formula I:

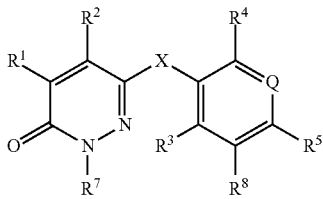

Formula I or a stereoisomer or a tautomer thereof, or a pharmaceutically acceptable salt thereof, wherein
- $R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens; or
- $R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens;
- $R^3$ and $R^4$ are each independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;
- $R^5$ is selected from:

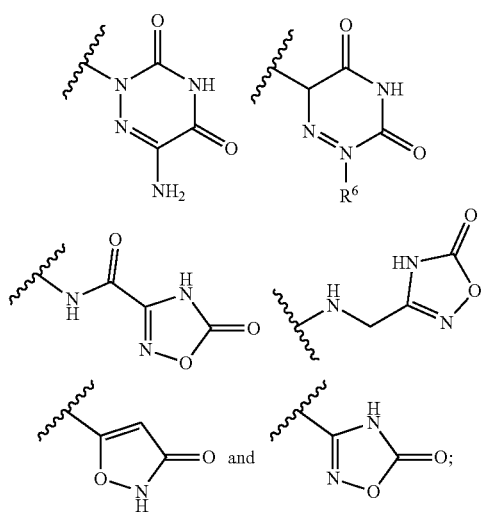

and

- $R^6$ is H or $C_1$-$C_3$ alkyl;
- $R^7$ is H or $C_1$-$C_3$ alkyl;
- $R^8$ is selected from H, halogen, —CN, optionally substituted $C_1$-$C_3$ alkyl, and optionally substituted $C_1$-$C_2$ alkoxy; or
- $R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;
- Q is selected from N, CH, and CF; and
- X is O or $CH_2$;
- wherein 0 to 10 hydrogen atoms that are attached to one or more carbon atoms are replaced with deuterium atom(s).

Embodiment P2. The compound of embodiment P1, or a stereoisomer or a tautomer thereof, or a pharmaceutically acceptable salt thereof, wherein $R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens.

Embodiment P3. The compound of embodiment P1 or embodiment P2, or a stereoisomer or a tautomer thereof, or a pharmaceutically acceptable salt thereof, wherein $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl.

Embodiment P4. The compound of embodiment P1 or embodiment P2, or a stereoisomer or a tautomer thereof, or a pharmaceutically acceptable salt thereof, wherein $R^1$ and $R^2$ together with the carbon atoms to which they are attached form a $C_4$-$C_7$ monocyclic ring optionally substituted with $C_3$-$C_5$ cycloalkyl optionally substituted with 1-3 halogens.

Embodiment P5. The compound of embodiment P1, or a stereoisomer or a tautomer thereof, or a pharmaceutically acceptable salt thereof, wherein $R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens.

Embodiment P6. The compound of any one of embodiments P1-P5, or a stereoisomer or a tautomer thereof, or a pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

Embodiment P7. The compound of any one of embodiments P1-P6, or a stereoisomer or a tautomer thereof, or a pharmaceutically acceptable salt thereof, wherein $R^3$ and $R^4$ are each independently selected from halogen and $C_1$-$C_3$ alkyl.

Embodiment P8. The compound of any one of embodiments P1-P7, or a stereoisomer or a tautomer thereof, or a pharmaceutically acceptable salt thereof, wherein $R^3$ and $R^4$ are both halogen.

Embodiment P9. The compound of any one of embodiments P1-P7, or a stereoisomer or a tautomer thereof, or a pharmaceutically acceptable salt thereof, wherein $R^3$ and $R^4$ are both methyl.

Embodiment P10. The compound of any one of embodiments P1-P9, or a stereoisomer or a tautomer thereof, or a pharmaceutically acceptable salt thereof, wherein $R^8$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

Embodiment P11. The compound of any one of embodiments P1-P5, or a stereoisomer or a tautomer thereof, or a pharmaceutically acceptable salt thereof, wherein $R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring.

Embodiment P12. The compound of any one of embodiments P1-P11, or a stereoisomer or a tautomer thereof, or a pharmaceutically acceptable salt thereof, wherein R⁵ is

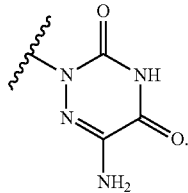 [SMILES: *n1nc(N)c(=O)[nH]c1=O]

Embodiment P13. The compound of any one of embodiments P1-P12, or a stereoisomer or a tautomer thereof, or a pharmaceutically acceptable salt thereof, wherein X is CH₂.

Embodiment P14. The compound of any one of embodiments P1-P12, or a stereoisomer or a tautomer thereof, or a pharmaceutically acceptable salt thereof, wherein X is O.

Embodiment P15. The compound of any one of embodiments P1-P14, or a stereoisomer or a tautomer thereof, or a pharmaceutically acceptable salt thereof, wherein R⁷ is H.

Embodiment P16. The compound of any one of embodiments P1-P14, or a stereoisomer or a tautomer thereof, or a pharmaceutically acceptable salt thereof, wherein R⁷ is $C_1$-$C_3$ alkyl.

Embodiment P17. The compound of any one of embodiments P1-P16, or a stereoisomer or a tautomer thereof, or a pharmaceutically acceptable salt thereof, wherein Q is CH.

Embodiment P18. The compound of any one of embodiments P1-P16, or a stereoisomer or a tautomer thereof, or a pharmaceutically acceptable salt thereof, wherein Q is N.

Embodiment P19. A compound selected from the group consisting of:
(R)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;
(S)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(4-chloro-5-((7-methyl-1-oxo-2,5,6,7-tetrahydro-1H-cyclopenta[d]pyridazin-4-yl)oxy)bicyclo[4.2.0]octa-1,3,5-trien-2-yl)-1,2,4-triazine-3,5(2H,4H)-dione;
6-amino-2-(3,5-dichloro-4-((7-methyl-1-oxo-2,5,6,7-tetrahydro-1H-cyclopenta[d]pyridazin-4-yl)oxy)phenyl-2,6-d2)-1,2,4-triazine-3,5(2H,4H)-dione;
6-amino-2-(5-((7-cyclopropyl-1-oxo-2,5,6,7-tetrahydro-1H-cyclopenta[d]pyridazin-4-yl)oxy)-4-methylbicyclo[4.2.0]octa-1,3,5-trien-2-yl)-1,2,4-triazine-3,5(2H,4H)-dione;
6-amino-2-(3,5-dichloro-4-((7-ethyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7-cyclopropyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7-(3,3-difluorocyclobutyl)-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((4'-oxo-3',4',6',7'-tetrahydrospiro[cyclopentane-1,5'-cyclopenta[d]pyridazin]-1'-yl)oxy)phenyl)-1,2,4-triazine-3,5(2H,4H)-dione;
6-amino-2-(3,5-dichloro-4-((4-oxo-3,4,6,7-tetrahydrospiro[cyclopenta[d]pyridazine-5,1'-cyclopropan]-1-yl)oxy)phenyl)-1,2,4-triazine-3,5(2H,4H)-dione;
6-amino-2-(3,5-dichloro-4-((4'-oxo-3',4',6',7'-tetrahydrospiro[cyclobutane-1,5'-cyclopenta[d]pyridazin]-1'-yl)oxy)phenyl)-1,2,4-triazine-3,5(2H,4H)-dione;
6-amino-2-(3,5-dichloro-4-((4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-methyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-ethyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-cyclopropyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5,5-dimethyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5,5-diethyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-oxo-3,4-diazabicyclo[4.2.0]octa-1(6),2-dien-2-yl)oxy)phenyl)-1,2,4-triazine-3,5(2H,4H)-dione;
6-amino-2-(3,5-dichloro-4-((1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7,7-dimethyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7,7-diethyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((4-oxo-3,4,4b,5,5a,6-hexahydrocyclopropa[3,4]cyclopenta[1,2-d]pyridazin-1-yl)oxy)phenyl)-1,2,4-triazine-3,5(2H,4H)-dione;
6-amino-2-(3,5-dichloro-4-((5-methyl-4-oxo-3,4,5,6,7,8-hexahydro-5,8-ethanophthalazin-1-yl)oxy)phenyl)-1,2,4-triazine-3,5(2H,4H)-dione;
6-amino-2-(3,5-dichloro-4-((9-methyl-1-oxo-2,5,6,7,8,9-hexahydro-1H-cyclohepta[d]pyridazin-4-yl)oxy)phenyl)-1,2,4-triazine-3,5(2H,4H)-dione;
6-amino-2-(3,5-dichloro-4-((7-methyl-1-oxo-2,5,6,7-tetrahydro-1H-cyclopenta[d]pyridazin-4-yl)oxy)phenyl-2-d)-1,2,4-triazine-3,5(2H,4H)-dione;
6-amino-2-(3,5-dichloro-4-((7-cyclopropyl-1-oxo-2,5,6,7-tetrahydro-1H-cyclopenta[d]pyridazin-4-yl)oxy)phenyl-2-d)-1,2,4-triazine-3,5(2H,4H)-dione;
6-amino-2-(3,5-dichloro-2-fluoro-4-((7-methyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(4-chloro-6-methyl-5-((7-methyl-1-oxo-2,5,6,7-tetrahydro-1H-cyclopenta[d]pyridazin-4-yl)oxy)pyridin-2-yl)-1,2,4-triazine-3,5(2H,4H)-dione; and
6-amino-2-(3,5-dichloro-4-((4-oxo-3,4,5,6,7,8-hexahydro-5,8-methanophthalazin-1-yl)oxy)phenyl)-1,2,4-triazine-3,5(2H,4H)-dione;
or a stereoisomer or a tautomer thereof, or a pharmaceutically acceptable salt thereof.

Embodiment P20. A pharmaceutical composition comprising the compound of any one of embodiments P1-P19, or the stereoisomer or the tautomer thereof, or the pharmaceutically acceptable salt thereof, and at least one pharmaceutically acceptable excipient.

Embodiment P21. A method of treating a disorder or disease in a subject in need thereof, the method comprising administering to the subject a therapeutically effective amount of the compound of any one of embodiments P1-P19, or the stereoisomer or the tautomer thereof, or the pharmaceutically acceptable salt thereof, or a therapeutically effective amount of the pharmaceutical composition of embodiment P20, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P22. Use of the compound of any one of embodiments P1-P19, or the stereoisomer or the tautomer thereof, or the pharmaceutically acceptable salt thereof, for the manufacture of a medicament for the treatment of a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P23. A compound of any one of embodiments P1-P19, or a stereoisomer or a tautomer thereof, or a pharmaceutically acceptable salt thereof, for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P24. A composition of embodiment P20 for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P25. A method of treating a thyroid hormone receptor related disorder in a patient, the method comprising the steps of:
identifying a patient in need of treatment for the thyroid hormone receptor related disorder, and
administering to the patient, or contacting the patient with, the compound of any one of embodiments P1-P19, or the stereoisomer or the tautomer thereof, or the pharmaceutically acceptable salt thereof, or a therapeutically effective amount of the pharmaceutical composition of embodiment P20.

Embodiment P26. The method of embodiment P25, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment P27. A method of selectively modulating the activity of a thyroid hormone receptor beta (THR-β) comprising contacting the compound of any one of embodiments P1-P19, or the stereoisomer or the tautomer thereof, or the pharmaceutically acceptable salt thereof, with the thyroid hormone receptor.

Embodiment P28. The method of embodiment P27, wherein the contacting is in vitro or ex vivo.

Embodiment P29. The method of embodiment P27, wherein the contacting is in vivo.

Embodiment P30. A compound of any one of embodiments P1-P19, or a stereoisomer or a tautomer thereof, or a pharmaceutically acceptable salt thereof, for use in selectively modulating the activity of a thyroid hormone receptor beta (THR-β).

Embodiment P31. A composition of embodiment P20 for use in selectively modulating the activity of a thyroid hormone receptor beta (THR-β).

ADDITIONAL EMBODIMENTS

Embodiment 1. A compound of Formula I:

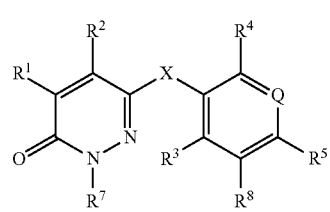

Formula I or a stereoisomer or a tautomer thereof, or a pharmaceutically acceptable salt thereof, wherein
$R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens; or
$R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens;
$R^3$ and $R^4$ are each independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;
$R^5$ is selected from:

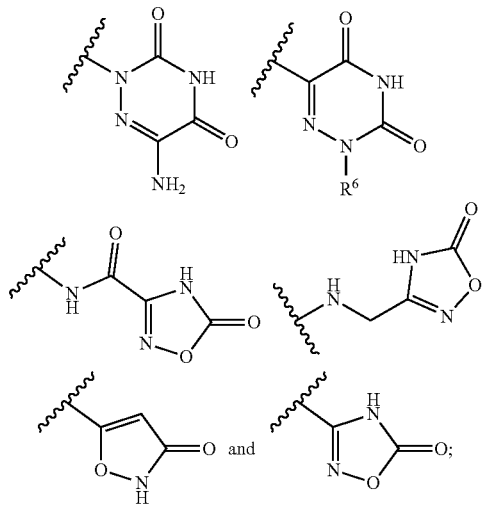

$R^6$ is H or $C_1$-$C_3$ alkyl;
$R^7$ is H or $C_1$-$C_3$ alkyl;
$R^8$ is selected from H, halogen, —CN, optionally substituted $C_1$-$C_3$ alkyl, and optionally substituted $C_1$-$C_2$ alkoxy; or
$R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;
Q is selected from N, CH, and CF; and
X is O or $CH_2$;

wherein when $R^1$ and $R^2$ together with the carbon atoms to which they are attached form a $C_6$ aromatic monocyclic ring, $R^5$ is selected from:

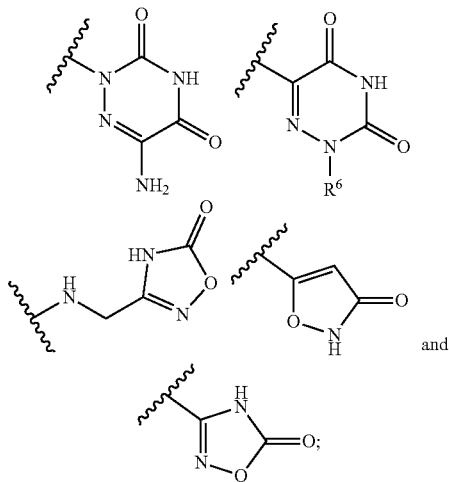

and
wherein 0 to 10 hydrogen atoms that are attached to one or more carbon atoms are replaced with deuterium atom(s).

Embodiment 2. The compound of embodiment 1, or a stereoisomer or a tautomer thereof, or a pharmaceutically acceptable salt thereof, wherein $R^1$ and $R^2$ together with the carbon atoms to which they are attached form a $C_4$-$C_7$ monocyclic ring optionally substituted with 1 to 3 substituents independently selected from halogen, $C_1$-$C_6$ alkyl, and $C_3$-$C_5$ cycloalkyl optionally substituted with 1-3 halogens.

Embodiment 3. The compound of embodiment 1 or embodiment 2, or a stereoisomer or a tautomer thereof, or a pharmaceutically acceptable salt thereof, wherein $R^1$ and $R^2$ together with the carbon atoms to which they are attached form a $C_4$-$C_7$ monocyclic ring optionally substituted with 1 to 3 substituents independently selected from halogen and $C_1$-$C_6$ alkyl.

Embodiment 4. The compound of embodiment 1 or embodiment 2, or a stereoisomer or a tautomer thereof, or a pharmaceutically acceptable salt thereof, wherein $R^1$ and $R^2$ together with the carbon atoms to which they are attached form a $C_5$ monocyclic ring optionally substituted with 1 to 3 substituents independently selected from halogen and $C_1$-$C_6$ alkyl.

Embodiment 5. The compound of embodiment 1 or embodiment 2, or a stereoisomer or a tautomer thereof, or a pharmaceutically acceptable salt thereof, wherein $R^1$ and $R^2$ together with the carbon atoms to which they are attached form a $C_6$ monocyclic ring optionally substituted with 1 to 3 substituents independently selected from halogen and $C_1$-$C_6$ alkyl.

Embodiment 6. The compound of embodiment 1 or embodiment 2, or a stereoisomer or a tautomer thereof, or a pharmaceutically acceptable salt thereof, wherein $R^1$ and $R^2$ together with the carbon atoms to which they are attached form a $C_4$-$C_7$ monocyclic ring optionally substituted with $C_3$-$C_5$ cycloalkyl optionally substituted with 1-3 halogens.

Embodiment 7. The compound of embodiment 1 or embodiment 2, or a stereoisomer or a tautomer thereof, or a pharmaceutically acceptable salt thereof, wherein $R^1$ and $R^2$ together with the carbon atoms to which they are attached form a $C_5$ monocyclic ring optionally substituted with $C_3$-$C_5$ cycloalkyl optionally substituted with 1-3 halogens.

Embodiment 8. The compound of embodiment 1 or embodiment 2, or a stereoisomer or a tautomer thereof, or a pharmaceutically acceptable salt thereof, wherein $R^1$ and $R^2$ together with the carbon atoms to which they are attached form a $C_6$ monocyclic ring optionally substituted with $C_3$-$C_5$ cycloalkyl optionally substituted with 1-3 halogens.

Embodiment 9. The compound of any one of embodiments 1-8, wherein the monocyclic ring is not aromatic.

Embodiment 10. The compound of embodiment 1, or a stereoisomer or a tautomer thereof, or a pharmaceutically acceptable salt thereof, wherein $R^1$ and $R^2$ together with the carbon atoms to which they are attached form a polycyclic ring optionally substituted with 1 to 3 substituents independently selected from halogen, $C_1$-$C_6$ alkyl, and $C_3$-$C_5$ cycloalkyl optionally substituted with 1-3 halogens.

Embodiment 11. The compound of any one of embodiments 1-10, or a stereoisomer or a tautomer thereof, or a pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

Embodiment 12. The compound of any one of embodiments 1-11, or a stereoisomer or a tautomer thereof, or a pharmaceutically acceptable salt thereof, wherein $R^3$ and $R^4$ are each independently selected from halogen and $C_1$-$C_3$ alkyl.

Embodiment 13. The compound of any one of embodiments 1-12, or a stereoisomer or a tautomer thereof, or a pharmaceutically acceptable salt thereof, wherein $R^3$ and $R^4$ are both halogen.

Embodiment 14. The compound of any one of embodiments 1-12, or a stereoisomer or a tautomer thereof, or a pharmaceutically acceptable salt thereof, wherein $R^3$ and $R^4$ are both methyl.

Embodiment 15. The compound of any one of embodiments 1-14, or a stereoisomer or a tautomer thereof, or a pharmaceutically acceptable salt thereof, wherein $R^8$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

Embodiment 16. The compound of any one of embodiments 1-14, or a stereoisomer or a tautomer thereof, or a pharmaceutically acceptable salt thereof, wherein $R^8$ is H.

Embodiment 17. The compound of any one of embodiments 1-10, or a stereoisomer or a tautomer thereof, or a pharmaceutically acceptable salt thereof, wherein $R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring.

Embodiment 18. The compound of any one of embodiments 1-16, or a stereoisomer or a tautomer thereof, or a pharmaceutically acceptable salt thereof, wherein $R^5$ is

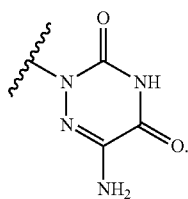 [SMILES: *n1nc(N)c(=O)[nH]c1=O]

Embodiment 19. The compound of any one of embodiments 1-18, or a stereoisomer or a tautomer thereof, or a pharmaceutically acceptable salt thereof, wherein X is $CH_2$.

Embodiment 20. The compound of any one of embodiments 1-18, or a stereoisomer or a tautomer thereof, or a pharmaceutically acceptable salt thereof, wherein X is O.

Embodiment 21. The compound of any one of embodiments 1-20, or a stereoisomer or a tautomer thereof, or a pharmaceutically acceptable salt thereof, wherein $R^7$ is H.

Embodiment 22. The compound of any one of embodiments 1-20, or a stereoisomer or a tautomer thereof, or a pharmaceutically acceptable salt thereof, wherein $R^7$ is $C_1$-$C_3$ alkyl.

Embodiment 23. The compound of any one of embodiments 1-22, or a stereoisomer or a tautomer thereof, or a pharmaceutically acceptable salt thereof, wherein Q is CH.

Embodiment 24. The compound of any one of embodiments 1-22, or a stereoisomer or a tautomer thereof, or a pharmaceutically acceptable salt thereof, wherein Q is N.

Embodiment 25. A compound selected from the group consisting of:

(R)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

(S)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(4-chloro-5-((7-methyl-1-oxo-2,5,6,7-tetrahydro-1H-cyclopenta[d]pyridazin-4-yl)oxy)bicyclo[4.2.0]octa-1,3,5-trien-2-yl)-1,2,4-triazine-3,5(2H,4H)-dione;

6-amino-2-(3,5-dichloro-4-((7-methyl-1-oxo-2,5,6,7-tetrahydro-1H-cyclopenta[d]pyridazin-4-yl)oxy)phenyl-2,6-d2)-1,2,4-triazine-3,5(2H,4H)-dione;

6-amino-2-(5-((7-cyclopropyl-1-oxo-2,5,6,7-tetrahydro-1H-cyclopenta[d]pyridazin-4-yl)oxy)-4-methylbicyclo[4.2.0]octa-1,3,5-trien-2-yl)-1,2,4-triazine-3,5(2H,4H)-dione;

6-amino-2-(3,5-dichloro-4-((7-ethyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7-cyclopropyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7-(3,3-difluorocyclobutyl)-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((4'-oxo-3',4',6',7'-tetrahydrospiro[cyclopentane-1,5'-cyclopenta[d]pyridazin]-1'-yl)oxy)phenyl)-1,2,4-triazine-3,5(2H,4H)-dione;

6-amino-2-(3,5-dichloro-4-((4-oxo-3,4,6,7-tetrahydrospiro[cyclopenta[d]pyridazine-5,1'-cyclopropan]-1-yl)oxy)phenyl)-1,2,4-triazine-3,5(2H,4H)-dione;

6-amino-2-(3,5-dichloro-4-((4'-oxo-3',4',6',7'-tetrahydrospiro[cyclobutane-1,5'-cyclopenta[d]pyridazin]-1'-yl)oxy)phenyl)-1,2,4-triazine-3,5(2H,4H)-dione;

6-amino-2-(3,5-dichloro-4-((4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-methyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-ethyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-cyclopropyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5,5-dimethyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5,5-diethyl-4-oxo-3,4,5,6,7,8-hexahydrophthalazin-1-yl)oxy)phenyl)-1,2,4-triazine-3,5(2H,4H)-dione;

6-amino-2-(3,5-dichloro-4-((5-oxo-3,4-diazabicyclo[4.2.0]octa-1(6),2-dien-2-yl)oxy)phenyl)-1,2,4-triazine-3,5(2H,4H)-dione;

6-amino-2-(3,5-dichloro-4-((1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7,7-dimethyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((7,7-diethyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(3,5-dichloro-4-((4-oxo-3,4,4b,5,5a,6-hexahydrocyclopropa[3,4]cyclopenta[1,2-d]pyridazin-1-yl)oxy)phenyl)-1,2,4-triazine-3,5(2H,4H)-dione;

6-amino-2-(3,5-dichloro-4-((5-methyl-4-oxo-3,4,5,6,7,8-hexahydro-5,8-ethanophthalazin-1-yl)oxy)phenyl)-1,2,4-triazine-3,5(2H,4H)-dione;

6-amino-2-(3,5-dichloro-4-((9-methyl-1-oxo-2,5,6,7,8,9-hexahydro-1H-cyclohepta[d]pyridazin-4-yl)oxy)phenyl)-1,2,4-triazine-3,5(2H,4H)-dione;

6-amino-2-(3,5-dichloro-4-((7-methyl-1-oxo-2,5,6,7-tetrahydro-1H-cyclopenta[d]pyridazin-4-yl)oxy)phenyl-2-d)-1,2,4-triazine-3,5(2H,4H)-dione;

6-amino-2-(3,5-dichloro-4-((7-cyclopropyl-1-oxo-2,5,6,7-tetrahydro-1H-cyclopenta[d]pyridazin-4-yl)oxy)phenyl-2-d)-1,2,4-triazine-3,5(2H,4H)-dione;

6-amino-2-(3,5-dichloro-2-fluoro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(4-chloro-6-methyl-5-((7-methyl-1-oxo-2,5,6,7-tetrahydro-1H-cyclopenta[d]pyridazin-4-yl)oxy)pyridin-2-yl)-1,2,4-triazine-3,5(2H,4H)-dione; and 6-amino-2-(3,5-dichloro-4-((4-oxo-3,4,5,6,7,8-hexahydro-5,8-methanophthalazin-1-yl)oxy)phenyl)-1,2,4-triazine-3,5(2H,4H)-dione;

or a stereoisomer or a tautomer thereof, or a pharmaceutically acceptable salt thereof.

Embodiment 26. A pharmaceutical composition comprising the compound of any one of embodiments 1-25, or the stereoisomer or the tautomer thereof, or the pharmaceutically acceptable salt thereof, and at least one pharmaceutically acceptable excipient.

Embodiment 27. A method of treating a disorder or disease in a subject in need thereof, the method comprising administering to the subject a therapeutically effective amount of the compound of any one of embodiments 1-25, or the stereoisomer or the tautomer thereof, or the pharmaceutically acceptable salt thereof, or a therapeutically effective amount of the pharmaceutical composition of embodiment 26, wherein the disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 28. Use of the compound of any one of embodiments 1-25, or the stereoisomer or the tautomer thereof, or the pharmaceutically acceptable salt thereof, for the manufacture of a medicament for the treatment of a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 29. A compound of any one of embodiments 1-25, or a stereoisomer or a tautomer thereof, or a pharmaceutically acceptable salt thereof, for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 30. A composition of embodiment 29 for use in treating a disorder or disease is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 31. A method of treating a thyroid hormone receptor related disorder in a patient, the method comprising the steps of:
identifying a patient in need of treatment for the thyroid hormone receptor related disorder, and
administering to the patient, or contacting the patient with, the compound of any one of embodiments 1-25, or the stereoisomer or the tautomer thereof, or the pharmaceutically acceptable salt thereof, or a therapeutically effective amount of the pharmaceutical composition of embodiment 26.

Embodiment 32. The method of embodiment 31, wherein the thyroid hormone receptor related disorder is selected from non-alcoholic steatohepatitis (NASH), obesity, hyperlipidemia, hypercholesterolemia, diabetes, liver steatosis, atherosclerosis, cardiovascular diseases, hypothyroidism, and thyroid cancer.

Embodiment 33. A method of selectively modulating the activity of a thyroid hormone receptor beta (THR-β) comprising contacting the compound of any one of embodiments 1-24, or the stereoisomer or the tautomer thereof, or the pharmaceutically acceptable salt thereof, with the thyroid hormone receptor.

Embodiment 34. The method of embodiment 33, wherein the contacting is in vitro or ex vivo.

Embodiment 35. The method of embodiment 33, wherein the contacting is in vivo.

Embodiment 36. A compound of any one of embodiments 1-25, or a stereoisomer or a tautomer thereof, or a pharmaceutically acceptable salt thereof, for use in selectively modulating the activity of a thyroid hormone receptor beta (THR-β).

Embodiment 37. A composition of embodiment 26 for use in selectively modulating the activity of a thyroid hormone receptor beta (THR-β).

Embodiment 38. The method of embodiments 27, 31 or 32, wherein the compound of any one of embodiments 1-25 or the stereoisomer or the tautomer thereof, or the pharmaceutically acceptable salt thereof, or a therapeutically effective amount of the pharmaceutical composition of embodiment 26, is administered in combination with a KHK inhibitor, an FXR agonist, a SSAO inhibitor, a FASN inhibitor, or a SCD1 modulator.

Embodiment 39. The method of embodiment 38, the KHK inhibitor is PF-06835919; the FXR agonist is TERN-101 (LY2562175), Tropifexor, obeticholic acid (OCA), or ASC42; the SSAO inhibitor is TERN-201; the FASN inhibitor is ASC40; and the SCD1 modulator is aramchol.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A compound of Formula I:

Formula I or a stereoisomer or a tautomer thereof, or a pharmaceutically acceptable salt thereof, wherein
$R^1$ and $R^2$ together with the carbon atoms to which they are attached form a $C_4$-$C_7$ non-aromatic monocyclic ring optionally substituted with 1 to 3 substituents independently selected from halogen, $C_1$-$C_6$ alkyl, and $C_3$-$C_5$ cycloalkyl optionally substituted with 1-3 halogens; or
$R^1$ and $R^2$ together with the carbon atoms to which they are attached form a $C_6$ aromatic monocyclic ring; or
$R^1$ and $R^2$ together with the carbon atoms to which they are attached form a non-aromatic polycyclic ring optionally substituted with 1 to 3 substituents independently selected from halogen, $C_1$-$C_6$ alkyl, and $C_3$-$C_5$ cycloalkyl optionally substituted with 1-3 halogens;
$R^3$ and $R^4$ are each independently selected from halogen, —CN, optionally substituted $C_1$-$C_3$ alkyl, optionally substituted $C_1$-$C_2$ alkoxy, optionally substituted $C_2$-$C_3$ alkenyl, and cyclopropyl;
$R^5$ is selected from:

$R^6$ is H or $C_1$-$C_3$ alkyl;
$R^7$ is H or $C_1$-$C_3$ alkyl;
$R^8$ is selected from H, halogen, —CN, optionally substituted $C_1$-$C_3$ alkyl, and optionally substituted $C_1$-$C_2$ alkoxy; or
$R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring;
Q is selected from N, CH, and CF; and
X is O or $CH_2$;
wherein when $R^1$ and $R^2$ together with the carbon atoms to which they are attached form a $C_6$ aromatic monocyclic ring, $R^5$ is selected from:

and
wherein 0 to 10 hydrogen atoms that are attached to one or more carbon atoms are replaced with deuterium atom(s).

2. The compound of claim 1, or a stereoisomer or a tautomer thereof, or a pharmaceutically acceptable salt thereof, wherein $R^1$ and $R^2$ together with the carbon atoms to which they are attached form a $C_4$-$C_7$ non-aromatic monocyclic ring optionally substituted with 1 to 3 substituents independently selected from halogen, $C_1$-$C_6$ alkyl, and $C_3$-$C_5$ cycloalkyl optionally substituted with 1-3 halogens.

3. The compound of claim 1, or a stereoisomer or a tautomer thereof, or a pharmaceutically acceptable salt thereof, wherein $R^1$ and $R^2$ together with the carbon atoms to which they are attached form a $C_5$ non-aromatic monocyclic ring optionally substituted with 1 to 3 substituents independently selected from halogen and $C_1$-$C_6$ alkyl.

4. The compound of claim 1, or a stereoisomer or a tautomer thereof, or a pharmaceutically acceptable salt thereof, wherein $R^1$ and $R^2$ together with the carbon atoms to which they are attached form a $C_4$-$C_7$ non-aromatic monocyclic ring optionally substituted with $C_3$-$C_5$ cycloalkyl optionally substituted with 1-3 halogens.

5. The compound of claim 1, wherein the monocyclic ring formed by $R^1$ and $R^2$ is not aromatic.

6. The compound of claim 1, or a stereoisomer or a tautomer thereof, or a pharmaceutically acceptable salt thereof, wherein $R^1$ and $R^2$ together with the carbon atoms to which they are attached form a non-aromatic polycyclic ring optionally substituted with 1 to 3 substituents independently selected from halogen, $C_1$-$C_6$ alkyl, and $C_3$-$C_5$ cycloalkyl optionally substituted with 1-3 halogens.

7. The compound of claim 1, or a stereoisomer or a tautomer thereof, or a pharmaceutically acceptable salt thereof, wherein $R^3$ and $R^4$ are each independently selected from halogen; —CN; $C_1$-$C_3$ alkyl optionally substituted with 1 to 3 substituents independently selected from halogen and $C_1$-$C_6$ alkoxy; $C_1$-$C_2$ alkoxy optionally substituted with 1 to 3 substituents independently selected from halogen; and $C_2$-$C_3$ alkenyl optionally substituted with 1 to 3 substituents independently selected from halogen and $C_1$-$C_6$ alkoxy; and cyclopropyl.

8. The compound of claim 1, or a stereoisomer or a tautomer thereof, or a pharmaceutically acceptable salt thereof, wherein $R^3$ and $R^4$ are both halogen.

9. The compound of claim 1, or a stereoisomer or a tautomer thereof, or a pharmaceutically acceptable salt thereof, wherein $R^8$ is selected from H; halogen; —CN; $C_1$-$C_3$ alkyl optionally substituted with 1 to 3 substituents independently selected from halogen and $C_1$-$C_2$ alkoxy; and $C_1$-$C_2$ alkoxy optionally substituted with 1 to 3 substituents independently selected from halogen.

10. The compound of claim 1, or a stereoisomer or a tautomer thereof, or a pharmaceutically acceptable salt thereof, wherein $R^3$ and $R^8$ together with the carbon atoms to which they are attached form a 4-, 5-, or 6-membered partially unsaturated carbocyclic ring; a 4-, 5-, or 6-membered partially unsaturated heterocyclic ring; a $C_6$-$C_{10}$ aryl ring; or a 5- or 6-membered heteroaryl ring.

11. The compound of claim 1, or a stereoisomer or a tautomer thereof, or a pharmaceutically acceptable salt thereof, wherein $R^5$ is

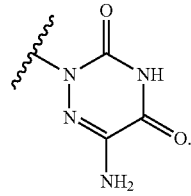 [SMILES: *n1nc(N)c(=O)[nH]c1=O]

12. The compound of claim 1, or a stereoisomer or a tautomer thereof, or a pharmaceutically acceptable salt thereof, wherein X is O.

13. The compound of claim 1, or a stereoisomer or a tautomer thereof, or a pharmaceutically acceptable salt thereof, wherein $R^7$ is H.

14. The compound of claim 1, or a stereoisomer or a tautomer thereof, or a pharmaceutically acceptable salt thereof, wherein Q is CH.

15. A compound selected from the group consisting of:
(R)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;
(S)-6-amino-2-(3,5-dichloro-4-((7-methyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(4-chloro-5-((7-methyl-1-oxo-2,5,6,7-tetrahydro-1H-cyclopenta[d]pyridazin-4-yl)oxy)bicyclo[4.2.0]octa-1,3,5-trien-2-yl)-1,2,4-triazine-3,5(2H,4H)-dione;
6-amino-2-(3,5-dichloro-4-((7-methyl-1-oxo-2,5,6,7-tetrahydro-1H-cyclopenta[d]pyridazin-4-yl)oxy)phenyl-2,6-d2)-1,2,4-triazine-3,5(2H,4H)-dione;
6-amino-2-(5-((7-cyclopropyl-1-oxo-2,5,6,7-tetrahydro-1H-cyclopenta[d]pyridazin-4-yl)oxy)-4-methylbicyclo[4.2.0]octa-1,3,5-trien-2-yl)-1,2,4-triazine-3,5(2H,4H)-dione;
6-amino-2-(3,5-dichloro-4-((7-ethyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7-cyclopropyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7-(3,3-difluorocyclobutyl)-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((4'-oxo-3',4',6',7'-tetrahydrospiro[cyclopentane-1,5'-cyclopenta[d]pyridazin]-1'-yl)oxy)phenyl)-1,2,4-triazine-3,5(2H,4H)-dione;
6-amino-2-(3,5-dichloro-4-((4-oxo-3,4,6,7-tetrahydrospiro[cyclopenta[d]pyridazine-5,1'-cyclopropan]-1-yl)oxy)phenyl)-1,2,4-triazine-3,5(2H,4H)-dione;
6-amino-2-(3,5-dichloro-4-((4'-oxo-3',4',6',7'-tetrahydrospiro[cyclobutane-1,5'-cyclopenta[d]pyridazin]-1'-yl)oxy)phenyl)-1,2,4-triazine-3,5(2H,4H)-dione;
6-amino-2-(3,5-dichloro-4-((4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-methyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-ethyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-cyclopropyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5,5-dimethyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5,5-diethyl-4-oxo-3,4,5,6,7,8-hexahydrophthalazin-1-yl)oxy)phenyl)-1,2,4-triazine-3,5(2H,4H)-dione;
6-amino-2-(3,5-dichloro-4-((5-oxo-3,4-diazabicyclo[4.2.0]octa-1(6),2-dien-2-yl)oxy)phenyl)-1,2,4-triazine-3,5(2H,4H)-dione;
6-amino-2-(3,5-dichloro-4-((1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7,7-dimethyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((7,7-diethyl-1-oxo-2,5,6,7-tetrahydro-1H-cyclopenta[d]pyridazin-4-yl)oxy)phenyl)-1,2,4-triazine-3,5(2H,4H)-dione;
6-amino-2-(3,5-dichloro-4-((4-oxo-3,4,4b,5,5a,6-hexahydrocyclopropa[3,4]cyclopenta[1,2-d]pyridazin-1-yl)oxy)phenyl)-1,2,4-triazine-3,5(2H,4H)-dione;
6-amino-2-(3,5-dichloro-4-((5-methyl-4-oxo-3,4,5,6,7,8-hexahydro-5,8-ethanophthalazin-1-yl)oxy)phenyl)-1,2,4-triazine-3,5(2H,4H)-dione;
6-amino-2-(3,5-dichloro-4-((9-methyl-1-oxo-2,5,6,7,8,9-hexahydro-1H-cyclohepta[d]pyridazin-4-yl)oxy)phenyl)-1,2,4-triazine-3,5(2H,4H)-dione;
6-amino-2-(3,5-dichloro-4-((7-methyl-1-oxo-2,5,6,7-tetrahydro-1H-cyclopenta[d]pyridazin-4-yl)oxy)phenyl-2-d)-1,2,4-triazine-3,5(2H,4H)-dione;
6-amino-2-(3,5-dichloro-4-((7-cyclopropyl-1-oxo-2,5,6,7-tetrahydro-1H-cyclopenta[d]pyridazin-4-yl)oxy)phenyl-2-d)-1,2,4-triazine-3,5(2H,4H)-dione;

6-amino-2-(3,5-dichloro-2-fluoro-4-((7-methyl-1-oxo-2,5,6,7-tetrahydro-1H-cyclopenta[d]pyridazin-4-yl)oxy)phenyl)-1,2,4-triazine-3,5(2H,4H)-dione;

6-amino-2-(4-chloro-6-methyl-5-((7-methyl-1-oxo-2,5,6,7-tetrahydro-1H-cyclopenta[d]pyridazin-4-yl)oxy)pyridin-2-yl)-1,2,4-triazine-3,5(2H,4H)-dione; and 6-amino-2-(3,5-dichloro-4-((4-oxo-3,4,5,6,7,8-hexahydro-5,8-methanophthalazin-1-yl)oxy)phenyl)-1,2,4-triazine-3,5(2H,4H)-dione;

or a stereoisomer or a tautomer thereof, or a pharmaceutically acceptable salt thereof.

16. A pharmaceutical composition comprising the compound of claim 1, or the stereoisomer or the tautomer thereof, or the pharmaceutically acceptable salt thereof, and at least one pharmaceutically acceptable excipient.

17. The compound of claim 12, wherein $R^1$ and $R^2$ together with the carbon atoms to which they are attached form a $C_6$ aromatic monocyclic ring, $R^5$ is

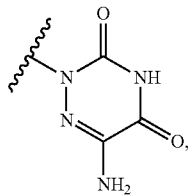 [SMILES: *n1nc(N)c(=O)[nH]c1=O]

$R^3$ and $R^4$ are both Cl, and $R^7$ and $R^8$ are both H.

18. The compound of claim 17, wherein the $C_6$ aromatic monocyclic ring is unsubstituted and Q is CH.

* * * * *